United States Patent [19]

Peake et al.

[11] Patent Number: 5,300,503
[45] Date of Patent: Apr. 5, 1994

[54] INSECTICIDAL 4,6-DIAMINO-1,2-DIHYDRO-1,3,5-TRIAZINE DERIVATIVES

[75] Inventors: Clinton J. Peake, Trenton; Thomas G. Cullen, Milltown; Albert C. Lew, Princeton Junction, all of N.J.

[73] Assignee: FMC Corporation, Philadelphia, Pa.

[21] Appl. No.: 786,498

[22] Filed: Nov. 1, 1991

[51] Int. Cl.⁵ ............... C07D 251/18; C07D 401/12; C07D 403/12; A01N 43/68
[52] U.S. Cl. .................... 514/245; 544/205; 544/206; 544/207
[58] Field of Search ................ 544/205, 206, 207; 514/245

[56] References Cited

U.S. PATENT DOCUMENTS

| 2,976,288 | 3/1961 | Green et al. | 260/249.9 |
|---|---|---|---|
| 3,105,074 | 9/1963 | Mamalis | 260/249.9 |
| 3,660,394 | 5/1972 | Mamalis | 260/249.9 |
| 3,682,912 | 8/1972 | Mamalis et al. | 260/249.9 |
| 3,723,429 | 3/1973 | Mamalis et al. | 260/249.9 |

FOREIGN PATENT DOCUMENTS

| 1053113 | 4/1963 | United Kingdom . |
|---|---|---|
| 1053307 | 4/1963 | United Kingdom . |
| 743964 | 6/1970 | United Kingdom . |
| 765176 | 8/1971 | United Kingdom . |
| 1297273 | 11/1972 | United Kingdom . |

OTHER PUBLICATIONS

Mamalis "Amino-oxy-derivatives. Part III. Dihydrotriazines and Related Heterocycles" J. Chem. Soc. (1962) 3915–26.
Mamalis "Aminooxy Derivatives. IV. Antimicrobial Activity of Some O-Ethers of 4,6-Diamino-1,2,-dihydro-1-hydroxy-2-substituted 1,3,5-Triazines" J. Med. Chem. (1965) 8, 684–91.
Mamalis "Amino-oxy-derivatives. Part V. Some O-Ethers of 2-Substituted 4,6-Diamino-1,2-dihydro-1-hydroxy-1,3,5-triazines" J. Chem. Soc. (1965) 1829–43.
Knight "The antimalarial activity of N-benzyl-oxydihydrotriazines" Ann. Trop. Med. and Paras. (1982) 76, No. 1 (1–7).
Mamalis "Amino-oxy-derivatives Part II. Some Derivatives of N-Hydroxydiguanide" J. Chem. Soc. (1962) 229–238.
Blaney, Jeffrey M., et al., Chemical Reviews (A.C.S.), vol. 84, No. 4 (1984), pp. 333–407.
Manteuffel-Cymborowska, Malgorzata, et al., J. Insect. Physiol. vol. 16, (1970), pp. 1419–1428.
Baker, B. R., J. Med. Chem., vol. 10 (1967), pp. 912–917.
Chmurzynska, Wanda, et al., Acta Biochemica Polonica, vol. 21, No. 4 (1974), pp. 445–453.

*Primary Examiner*—John M. Ford
*Attorney, Agent, or Firm*—Stanford M. Back; Robert M. Kennedy

[57] ABSTRACT

Insects, and particularly the larvae of Lepidoptera and Coleoptera, are controlled by application of 4,6-diamino-1,2-dihydro-dihydro-1,3,5-trazine derivatives, and agriculturally acceptable salts thereof, having the following structure;

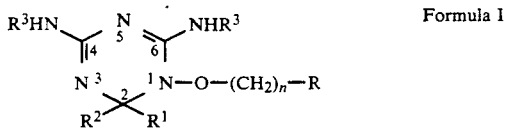

Formula I when they are admixed with a compatible agricultural vehicle; additionally, certain related novel heterocyclyl, phenyl, and naphthyl triazines and their substituted counterparts are also taught.

40 Claims, No Drawings

INSECTICIDAL 4,6-DIAMINO-1,2-DIHYDRO-1,3,5-TRIAZINE DERIVATIVES

BACKGROUND OF THE INVENTION

This invention relates to certain chemical compounds and compositions containing the same which are useful for controlling insects in agricultural crops. More particularly, this invention relates to certain 1,3,5-triazine compounds and compositions, and their use as insecticides against a variety of insects, especially those of the order Lepidoptera and Coleoptera.

DESCRIPTION OF RELATED ART

Numerous of the triazine compounds employed in the compositions of this invention and their preparation, have been described in the literature for use in a variety of fields, but not as insecticides.

Thus, British Patents 1,053,113 and 1,053,307 disclose diamino-1,3,5-triazines as hypotensives, vasodilators, and CNS agents; British application BE 765,176 discloses like triazine derivatives as antimalarial or antimicrobial agents, as does BE 743,964.

Additionally, preparation and use of triazine compounds used in the compositions of this invention are disclosed in U.S. Pat. Nos. 2,976,288 (bactericides); 3,105,074 (bactericide intermediates); 3,660,394 (antiparasites); 3,682,912 (antimalarials); 3,723,429 (antimalarials); and British Patent 1,297,273 (antimalarials).

Mamalis et al have also written extensively concerning the antimicrobial and antimalarial properties of these triazines and their derivatives. See, for example, Mamalis et al, "Dihydrotriazines and Related Heterocycles", J. Chem. Soc. (London), 1962, 3915; "Antimicrobial Activity of Some O-Ethers of 4,6-Diamino-1,2-dihydro-1-hydroxy-2-substituted 1,3,5-Triazines", J. Med. Chem., 8, 684–91 (1965); (ibid) J. Chem. Soc., 1829–43 (1965); and "The Anti-Malaria Activity of N-Benzyloxy Dihydrotriazines", Annals of Tropical Medicine and parasitology, 76, No. 1 (1982).

See also, "Amino-Oxy Derivatives. Part III. Dihydrotriazines and Related Heterocycles", Mamalis et al., J. Chem. Soc. (London), 1962, p. 3915, and "Amino-Oxy Derivatives. Part II. Some Derivatives of N-Hydroxydiguanide", Mamalis et al., J. Chem. Soc. (London), 1962, p. 229, which further disclose methods for making these compounds.

None of these patents or literature references suggests the use of these dihydrotriazine derivatives as insecticides, some of which are effective in doses of as little as about 1 ppm.

SUMMARY OF THE INVENTION

In accordance with the present invention it has been found that 4,6-diamino-1,2-dihydro-1,3,5-triazine derivatives, and agriculturally acceptable salts thereof, which are useful as active ingredients in the compositions and methods of this invention, may be represented by the following structure:

$$R^3HN-\underset{N^3}{\overset{N^5}{C_4}}\underset{R^2}{\overset{C_6}{\underset{R^1}{C_2}}}NHR^3 \quad \text{Formula I}$$
$$N^1-O-(CH_2)_n-R$$

wherein R is selected from the group consisting of hydrogen, straight or branched chain alkyl, haloalkyl, (substituted aryl)haloalkyl, arylalkyl, (substituted aryl)alkyl, (α-cycloalkyl)arylalkyl, cycloalkyl, arylcycloalkyl, (substituted aryl)cycloalkyl, alkenyl, cycloalkenyl, arylalkenyl, (substituted aryl)alkenyl, alkynyl, arylalkynyl, (substituted aryl)alkynyl, alkoxy, (substituted aryl)alkoxy, aryl, aryloxy, (substituted aryl)oxy, arylthio, (substituted aryl)thio, heterocyclyl, alkoxycarbonyl, and substituted aryl of the structure

[structure showing benzene ring with substituents V, W, X, Y, Z]

wherein
V, W, X, Y, and Z are independently selected from the group consisting of hydrogen, halogen, lower alkyl, haloalkyl, cycloalkyl, arylalkyl, alkoxy, haloalkoxy, arylalkoxy, aryl (e.g. biphenyl), substituted aryl (e.g. substituted biphenyl), aryloxy, (substituted aryl)oxy, alkylthio, alkylsulfoxy, alkylsulfonyl, cyano, and nitro;
V and W, or W and X, when taken together, comprise the ring-forming group $$-\underset{V'}{C}=\underset{W'}{C}-\underset{X'}{C}=\underset{Y'}{C}-,$$

(such as naphthyl or substituted naphthyl), wherein V', W', X' and Y' have the same definition as V, W, X, and Y (above);
n is 1 to 5;
$R^1$ is selected from the group consisting of lower alkyl, arylalkyl, arylalkenyl, and alkoxyaryl;
$R^2$ is selected from the group consisting of hydrogen, and lower alkyl, preferably methyl;
$R^1$ and $R^2$ may be taken together to form a spirocycloalkane ring;
$R^3$ is selected from the group consisting of hydrogen, lower alkylcarbonyl, cyclopropylcarbonyl, methoxymethylcarbonyl, and 2-furanylcarbonyl;
and agriculturally acceptable salts thereof. It will be understood that where applicable, these compounds also encompass their cis- and trans- forms.

Of these compounds, among the more preferred ones for use in the compositions and methods of this invention are those wherein R is cycloalkyl (including adamantyl); aryl (such as naphthyl); substituted phenoxy (preferably alkyl); substituted phenylthio (preferably halo); or substituted phenyl of the structure

[structure showing benzene ring with substituents V, W, X, Y, Z]

wherein
V, W, X, Y, and Z are independently halogen, or alkoxy, wherein at least one of V to Z is not hydrogen;
n is 1 to 4;

$R^1$ is methyl or ethyl;
$R^2$ is methyl; and $R^3$ is hydrogen,
or acid salts thereof.

Particularly preferred amongst the above compounds which may be employed in this invention are those which correspond to certain of the numbered compounds in Table 1 below; i.e., those where R is di- or tri-alkylphenoxy, such as Compounds 124, 191, 192 and 196 of Table 1 below; halophenyl such as Compounds 144, 146, 147, 205, and 217; or halophenylthio, such as Compound 127.

Also preferred are those where R is cycloalkyl, (e.g. Compound 113 or 201); 1-alkoxyphenyl(alkyl), (e.g. Compound 116); or aryl (e.g. Compound 166).

Illustrative of the more preferred of these compounds, corresponding to those of Table 1 below, are the following:

| | |
|---|---|
| Cmpd 113 | 4,6-diamino-1,2-dihydro-2,2-dimethyl-1-cycloheptylmethoxy-1,3,5-triazine hydrobromide; |
| Cmpd 116 | 4,6-diamino-1,2-dihydro-2,2-dimethyl-1-[3-(4-methoxyphenyl)butoxy]-1,3,5-triazine hydrobromide; |
| Cmpd 124 | 4,6-diamino-1,2-dihydro-2,2-dimethyl-1-[3-(2,4,6-trimethylphenoxy)propoxy]-1,3,5-triazine hydrobromide; |
| Cmpd 127 | 4,6-diamino-1,2-dihydro-2,2-dimethyl-1-(4-chlorophenylthiomethoxy)-1,3,5-triazine hydrochloride; |
| Cmpd 144 | 4,6-diamino-1,2-dihydro-2,2-dimethyl-1-[3-(2,6-dichlorophenyl)propoxy]-1,3,5-triazine hydrobromide; |
| Cmpd 146 | 4,6-diamino-1,2-dihydro-2,2-dimethyl-1-(2,4,5-trichlorophenylmethoxy)-1,3,5-triazine, pamoic acid salt; |
| Cmpd 147 | 4,6-diamino-1,2-dihydro-2,2-dimethyl-1-(5-bromo-2,4-dichlorophenylmethoxy)-1,3,5-triazine, pamoic acid salt; |
| Cmpd 166 | 4,6-diamino-1,2-dihydro-2,2-dimethyl-1-(naphth-1-ylmethoxy)-1,3,5-triazine, pentanoic acid salt; |
| Cmpd 191 | 4,6-diamino-1,2-dihydro-2,2-dimethyl-1-[3-(2,4-dimethylphenoxy)propoxy]-1,3,5-triazine hydrobromide; |
| Cmpd 192 | 4,6-diamino-1,2-dihydro-2,2-dimethyl-1-[3-(2,5-dimethylphenoxy)propoxy]-1,3,5-triazine hydrobromide; |
| Cmpd 196 | 4,6-diamino-1,2-dihydro-2,2-dimethyl-1-[3-(2,3,5-trimethylphenoxy)propoxy]-1,3,5-triazine hydrobromide; |
| Cmpd 201 | 4,6-diamino-1,2-dihydro-2,2-dimethyl-1-[2-(adamant-1-yl)ethoxy]-1,3,5-triazine hydrobromide; |
| Cmpd 205 | 4,6-diamino-1,2-dihydro-2,2-dimethyl-1-(4-bromophenylmethoxy)-1,3,5-triazine hydrobromide; |
| Cmpd 217 | 4,6-diamino-1,2-dihydro-2,2-dimethyl-1-[3-(2-bromo-4,5-dichlorophenyl)propoxy]-1,3,5-triazine hydrochloride. |

Each of these above compounds is preferred because they were all highly effective at low dosages.

For purposes of this invention, as regards the above substituent groups, the following definitions apply. The term alkyl includes straight or branched chain alkyl of from 1 to 13 carbon atoms, preferably 4 to 8 carbon atoms; alkenyl includes 2 to 13 carbon atoms, preferably 4 to 8 carbon atoms; while halogen includes chlorine, bromine, and fluorine atoms. The terms haloalkyl and haloalkoxy include branched or straight chain $C_{1-13}$ alkyl groups wherein one or more hydrogen atoms have been replaced with halogen atoms. The cycloalkyl groups, including any cis and trans forms, and which may be saturated or unsaturated, as for example hexyl or hexenyl, desirably contain from 3 to 7 carbon atoms and may be substituted by halogen, alkyl, substituted aryl, cyano, or the like. The terms aryl and substituted aryl include phenyl, naphthyl, and phenanthryl, preferably phenyl or substituted phenyl. The term substituted aryl includes those aryl groups substituted with one or more alkyl, halo, alkoxy, cycloalkyl, aryl, haloalkyl, haloalkoxy, cyano, nitro, dialkylamino, thioalkyl, or like moieties. The terms arylalkyl, arylcycloalkyl, and (α-cycloalkyl)arylalkyl, particularly as applied to the R group, include phenylalkyl, where the alkyl group may be straight or branched; and phenylcycloalkyl. Illustrations of these compounds include Compounds 117, 171, 178, 179 and 180 of Table 1 (below).

The term heterocyclic as employed herein includes thienyl, furyl, pyranyl, triazinyl, pyrrolyl, imidazolyl, pyridyl, pyridazinyl, isoxazolyl groups, and the like. Also included in the definition of heterocyclic substituents are those 5- and 6-member rings which are fused with an aryl group, typically phenyl, to form such heterocyclic groups as benzothienyl, isobenzofuranyl, indolyl, quinolyl, and the like. In addition, as shown in the examples below, R may also include such heterocyclic substituents as phthalimido, benzodioxolyl, benzodioxanyl, benzofuranyl, and benzopyranyl triazine derivatives.

Spirocycloalkanes include those having from 3 to 9 carbon atoms in their cycloalkane group, for example, spirocyclohexane.

As aforestated, the present 1,3,5-triazine compounds, when admixed with suitable carriers and applied to insect-infected crops such as cotton, tobacco, corn, and cole, are highly effective in controlling such insects as the larvae of the order Lepidoptera and Coleoptera, for example the tobacco budworm, beet armyworm, cabbage looper, corn earworm, diamondback moth, Mexican bean beetle, and the like. Uniquely, many of these compositions are highly effective at very low dosages, in contrast to known insecticides for this purpose, such as methomyl, which latter compound must be applied in higher amounts to provide equal effect.

In a further embodiment of this invention there are also contemplated certain classes of novel compounds per se which fall within the scope of Formula I (above), and which have insecticidal activity as described above.

Amongst them are included substituted triazine compounds of the formula

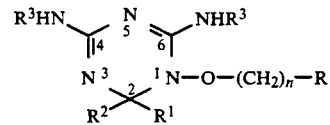

and agriculturally acceptable salts thereof, wherein R is a heterocyclyl moiety selected from the following

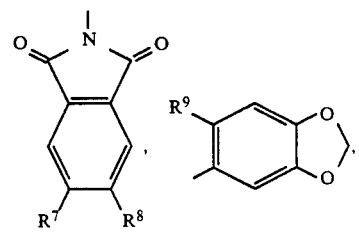

-continued

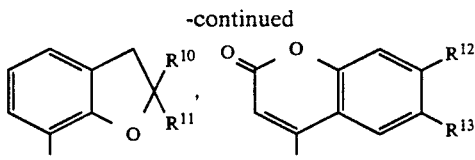

wherein
- R¹ is selected from the group consisting of lower alkyl, arylalkyl, arylalkenyl, and alkoxyaryl;
- R² is selected from the group consisting of hydrogen and methyl, and
- R¹ and R² may be taken together to form a spirocycloalkane ring;
- R³ is selected from the group consisting of hydrogen, lower alkylcarbonyl, cyclopropylcarbonyl, methoxymethylcarbonyl, and 2-furanylcarbonyl; and
- R⁷, R⁸, R⁹, R¹⁰, R¹¹, R¹², and R¹³ are independently hydrogen, halogen, alkyl, or alkoxy with the proviso that both of R⁷ and R⁸ may not be hydrogen and with the further proviso that R⁹ may not be hydrogen.

Typical illustrations of these novel compounds are the heterocyclyl- and substituted heterocyclyl-triazines exemplified by Compounds 35–37, and 130–132 of Table I below.

In yet another embodiment there are also contemplated certain other novel derivatives of the 1,3,5-triazines within Formula I (above) which are also useful as insecticides in the manner described below, and as antimalarial and antimicrobial compounds. Illustrative of these are Compounds 114–117, and 171–180 of Table I, below, and which have the formula

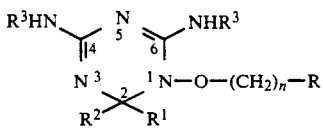

and agriculturally acceptable salts thereof, wherein R is selected from phenyl or naphthyl, phenylalkyl, phenylmethylalkyl, (α-cycloalkyl)phenylmethyl, or (phenyl-substituted)cycloalkyl wherein each phenyl or naphthyl group may optionally be substituted with lower alkyl, halogen, and lower alkoxy and each alkyl may be straight or branched;
- n is 1 to 5;
- R¹ is selected from the group consisting of lower alkyl, arylalkyl, arylalkenyl, and alkoxyaryl;
- R² is selected from the group consisting of hydrogen and methyl, and
- R¹ and R² may be taken together to form a spirocycloalkane ring; and
- R³ is selected from the group consisting of hydrogen, lower alkylcarbonyl, cyclopropylcarbonyl, methoxymethylcarbonyl, and 2-furanylcarbonyl, with the proviso that R³ is not hydrogen or lower alkylcarbonyl when R is (optionally substituted)phenyl, (optionally substituted)naphthyl, or phenylalkyl.

Each of the novel compounds of these additional embodiments may be prepared in the same or similar manner as those compounds of Formula I above.

DETAILED DESCRIPTION OF THE INVENTION

Synthesis of The Compounds

The compounds employed as insecticides in accordance with this invention are generally known to those skilled in the art, or may readily be prepared from these compounds by known methods. See, for example, the Mamalis et al. articles above. These and other methods are described in further detail in the examples below.

Thus, for example, using modified methods of Mamalis et al. (supra), 1-(alkoxy or arylalkoxy)diguanide may be prepared. Cyclization of this diguanide with an aldehyde or a ketone, e.g., acetone, in the presence of concentrated hydrochloric acid gives the corresponding dihydrotriazine hydrochloride. Examples of this salt prepared in this manner are 4,6-diamino-1,2-dihydro-2,2-dimethyl-1-(naphth-1-ylmethoxy)-1,3,5-triazine hydrochloride (Compound 92 below) and 4,6-diamino-1,2-dihydro-2,2-dimethyl-1-phenylmethoxy-1,3,5-triazine hydrochloride (Compound 37 below). This procedure is outlined in detail in Example 1.

The compounds of the present invention may conveniently be prepared in the form of the mono-acid addition salts which may be formed from a wide range of acids. When this occurs, the acid is usually an inorganic acid such as a hydrohalic acid, sulfuric acid, nitric acid and the like, preferably hydrochloric or hydrobromic acid. The acid addition salts tend to be greater in stability than the parent free-base, and so may be made with advantage.

However, salts may be made by simple reaction of the parent compounds with acid subsequent to their formation and isolation. Inorganic acids (such as those above) or organic acids may be used. Suitable organic acids include picric, acetic, maleic, phthalic, succinic, para-nitrobenzoic, stearic, mandelic, pamoic, citric, tartaric, alkylsulphonic, barbituric, or gluconic acid; (see e.g., Example 8), or sulfamethoxypyridazine salts.

The free-base may optionally be reacted with a salt-forming acid, for example, nonanoic acid, yielding the corresponding salt. Examples of such salts prepared in this manner are 4,6-diamino-1,2-dihydro-2,2-dimethyl-1-(naphth-1-ylmethoxy)-1,3,5-triazine nonanoic acid salt (Compound 93 below) and the corresponding tetradecanoic acid salt (Compound 94 below).

In a method for preparing 4,6-di(substituted amino) derivatives of the hydrochloride salt, the free-base of the salt may be prepared by reaction of the salt with sodium carbonate in an appropriate solvent. The free-base may then in turn be reacted in-situ with two equivalents of an acid halide, for example, 2-furanoyl chloride, in the presence of an acid acceptor, yielding the corresponding 4,6-di(substituted-amino) derivatives of the hydrochloride salt. An example of the 4,6-di(substituted-amino) derivative of the salt is 4,6-di(furan-2-ylcarbonylamino)-1,2-dihydro-2,2-dimethyl-1-(naphth-1-ylmethoxy)-1,3,5-triazine (Compound 106 below). The preparation of the corresponding 4,6-di(substituted amino) derivatives is presented in detail in Example 7.

Where the salt is obtained first, the free-base of the salt may also be obtained by its treatment with a strongly basic gel-type resin in ethanol and water. An example of the free-base is 4,6-diamino-1,2-dihydro-2,2-dimethyl-1-(naphth-1-ylmethoxy)-1,3,5-triazine (Compound 95 below). This procedure to the free-base is presented in detail in Example 2.

Additional dihydrotriazine hydrohalide salts are prepared using a method described in U.S. Pat. No. 3,723,429. Using this method, a 1-(arylalkoxy)triazine hydrochloride, for example, 4,6-diamino-1,2-dihydro-2,2-dimethyl-1-phenylmethoxy-1,3,5-triazine hydrochloride (Compound 37 below) is prepared, as previously described, and hydrogenolyzed in ethanol in the presence of 10% platinium oxide on charcoal, affording the corresponding 1-hydroxytriazine hydrochloride. The 1-hydroxytriazine hydrochloride, for example 4,6-diamino-1,2-dihydro-1-hydroxy-2,2-dimethyl-1,3,5-triazine hydrochloride is then converted to the free-base by methods previously described and in turn may be reacted with an appropriately substituted halide, for example, 2,4,5-trichlorophenylmethyl bromide, in dimethylformamide, yielding the corresponding dihydrotriazine hydrohalide. The halide moiety of the substituted halide chosen to react with the 1-hydroxytriazine governs which hydrohalide salt is obtained. Examples of salts prepared in this manner are 4,6-diamino-1,2-dihydro-1-(2,4,5-trichlorophenylmethoxy)-2,2-dimethyl-1,3,5-triazine hydrobromide (Compound 60 below), and 4,6-diamino-1,2-dihydro-2,2-dimethyl-1-[2-(naphth-1-yl)ethoxy]-1,3,5-triazine hydrobromide (Compound 98 below). The procedure described in U.S. Pat. No. 3,723,429 is presented in detail in Examples 3 and 4.

The following examples, which disclose the preparation of representative compounds of this invention (Table 1, Compounds 92, 95, 60, 98, 99, 16, 106, and 146 corresponding to Examples 1–8, respectively), are for the purpose of illustrating known methods for the preparation of the compounds employed in the methods and formulations of this invention.

EXAMPLE 1

SYNTHESIS OF 4,6-DIAMINO-1,2-DIHYDRO-2,2-DIMETHYL-1-(NAPHTH-1-YLMETHOXY)-1,3,5-TRIAZINE HYDROCHLORIDE (COMPOUND 92)

Step A: Synthesis of 1,1-dimethylethyl N-hydroxycarbamate as an intermediate

A mixture of 49.1 grams (0.225 mole) of di(1,1-dimethylethyl) dicarbonate and 15.6 grams (0.225 mole) of hydroxylamine in 150 ml of methanol was stirred, and a solution of 32.9 ml (0.236 mole) of triethylamine in 60 ml of methanol was added dropwise. Upon completion of addition, the reaction mixture was stirred for one hour and then was concentrated under reduced pressure to a residue. The residue was extracted with 300 ml of diethyl ether. The ether extract was washed with 50 ml of aqueous 1N hydrochloric acid and then with two 50 ml portions of water. The organic layer was concentrated under reduced pressure, yielding 22.9 grams of 1,1-dimethylethyl N-hydroxycarbamate. The NMR spectrum was consistent with the proposed structure.

Step B: Synthesis of 1,1-dimethylethyl N-(naphth-1-ylmethoxy)carbamate as an intermediate Under a nitrogen atmosphere, a suspension of 1.6 grams (0.041 mole) of 60% sodium hydride (in mineral oil) in dimethylformamide was stirred, and 5.4 grams (0.041 mole) of 1,1-dimethylethyl N-hydroxycarbamate was carefully added portionwise. Upon completion of the evolution of hydrogen, 5.8 grams (0.032 mole) of naphth-1-ylmethyl chloride was added. Upon completion of addition, the reaction mixture was stirred for about 30 minutes. After this time the reaction mixture was poured into 200 ml of water. The mixture was extracted with 200 ml of diethyl ether. The ether extract was washed with three 50 ml portions of water. The organic layer was concentrated under reduced pressure to a residual oil. The oil was purified by column chromatography on silica gel. Elution was accomplished with mixtures of 5% to 20% diethyl ether in petroleum ether. The appropriate fractions were combined and concentrated under reduced pressure, yielding 3.4 grams of 1,1-dimethylethyl N-(naphth-1-ylmethoxy)-carbamate. The NMR spectrum was consistent with the proposed structure.

Step C: Synthesis of (naphth-1-ylmethoxy)amine hydrochloride as an intermediate

A solution of 3.4 grams (0.012 mole) of 1,1-dimethylethyl N-(naphth-1-ylmethoxy)carbamate in 30 ml of ethanol was stirred, and dry hydrogen chloride gas was bubbled into the solution during a 1 minute period. After this time, thin layer chromatographic analysis of the reaction mixture indicated that the reaction had gone to completion. The reaction mixture was concentrated under reduced pressure, yielding 2.5 grams of (naphth-1-ylmethoxy)amine hydrochloride; m.p. 193°–195° C. (Lit. m.p. 198° C.).

Step D: Synthesis of 1-(naphth-1-ylmethoxy)diguanide as an intermediate

Under a nitrogen atmosphere, a stirred solution of 2.5 grams (0.012 mole) of (naphth-1-ylmethoxy)amine hydrochloride and 1.2 grams (0.014 mole) of cyanoguanidine in 15 ml of ethanol was heated at reflux during a 2 hour period. To promote purification, the dihydrochloride salt of the reaction product was prepared by bubbling hydrogen chloride gas into the reaction mixture during a 30 second period. The reaction mixture was then taken up in an additional 7 ml of ethanol and 75 ml of diethyl ether. The resultant solid was collected by filtration and dried. The solid was dissolved in water and treated with a solution of 2.8 grams (0.020 mole) of potassium carbonate in 10 ml of water. The resultant solid was collected by filtration and dried under vacuum, yielding 1.9 grams of 1-(naphth-1-ylmethoxy)-diguanide; m.p. 147°–149° C. (lit. m.p. 145° C.). The NMR spectrum was consistent with the proposed structure.

Step E: Synthesis of 4,6-diamino-1,2-dihydro-2,2-dimethyl-1-(naphth-1-ylmethoxy)-1,3,5-triazine hydrochloride (Compound 92)

Under a nitrogen atmosphere, a stirred solution of 1.3 grams (0.005 mole) of 1-(naphth-1-ylmethoxy) diguanide and 0.42 ml (0.005 mole) of concentrated hydrochloride acid in 150 ml of acetone was heated at reflux for six hours. After this time the reaction mixture was concentrated under reduced pressure to a residual oil. Following unsuccessful attempts to crystallize the oil, it was redissolved in 150 ml of acetone, and 0.42 ml of concentrated hydrochloric acid was added. The solution slowly became cloudy and some crystals formed. The mixture was briefly heated to reflux, and then it was allowed to cool to ambient temperature where it was stirred for about 60 hours. The resultant solid was collected by filtration, yielding 1.3 grams of 4,6-diamino-1,2-dihydro-2,2-dimethyl-1-(naphth-1-ylmethoxy)-1,3,5-triazine hydrochloride; m.p. 217°–218° C. (lit. m.p. 215° C.). The NMR spectrum was consistent with the proposed structure.

EXAMPLE 2

SYNTHESIS OF 4,6-DIAMINO-1,2-DIHYDRO-2,2-DIMETHYL-1-(NAPHTH-1-YLMETHOXY)-1,3,5-TRIAZINE (COMPOUND 95)

A solution of 0.8 gram (0.002 mole) of 4,6-diamino-1,2-dihydro-1-(naphth-1-ylmethoxy)-2,2-dimethyl-1,3,5-triazine hydrochloride in about 10 ml of 1:1-water-ethanol was passed slowly though a 2.25 cm diameter column containing 10 ml of a strongly basic gel-type ion-exchange resin (sold under the trademark Amberlite ® IRA-400 (OH) ion-exchange resin). An additional 25 ml of 1:1-water-ethanol was passed through the column to remove the maximum amount of product. The combined eluants were cooled in a freezer, and the resultant solid was collected by filtration. The solid was dried, yielding 0.3 gram of 4,6-diamino-1,2-dihydro-2,2-dimethyl-1-(naphth-1-ylmethoxy)-1,3,5-triazine; m.p. 170°-171° C. (lit. m.p. 168°-170° C.). The NMR spectrum was consistent with the proposed structure.

EXAMPLE 3

SYNTHESIS OF 4,6-DIAMINO-1,2-DIHYDRO-2,2-DIMETHYL-1-(2,4,5-TRICHLOROPHENYLMETHOXY)-2,2-DIMETHYL-1,3,5-TRIAZINE HYDROBROMIDE (COMPOUND 60)

Step A Synthesis of 1-phenylmethoxydiguanide as an intermediate

This compound was prepared in a manner analogous to that of Example 1, Step D, using 100 grams (0.63 mole) of phenylmethoxyamine hydrochloride (commercially available) and 65 grams (0.77 mole) of cyanoguanidine in 200 ml of ethanol. This procedure differed from Example 1, Step D, in that the dihydrochloride salt was not prepared. Following treatment with potassium carbonate in water, the reaction mixture was extracted with 300 ml of ethyl acetate. The extract was concentrated under reduced pressure, yielding 120.1 grams of 1-phenylmethoxydiguanide; m.p.; 95°-100° C.

Step B: Synthesis of 4,6-diamino-1,2-dihydro-1-phenylmethoxy-2,2-dimethyl-1,3,5-triazine hydrochloride (Compound 37) for insecticidal testing and as an intermediate This compound was prepared in a manner analogous to that of Example 1, Step E, using 120.1 grams (0.58 mole) of 1-phenylmethoxydiguanide, 95 ml of concentrated hydrochloric acid, and 400 ml of acetone in 400 ml of ethanol. The reaction mixture was concentrated under reduced pressure to near-dryness. The concentrate was mixed with a hot mixture of 50 ml of ethanol in 400 ml of acetone. The resultant solid was collected by filtration, yielding 96.5 grams of 4,6-diamino-1,2-dihydro-1-phenylmethoxy-2,2-dimethyl-1,3,5-triazine hydrochloride, m.p. 218°-219° C. The NMR spectrum was consistent with the proposed structure.

Step C: Synthesis of 4,6-diamino-1,2-dihydro-1-hydroxy-2,2-dimethyl-1,3,5-triazine hydrochloride as an intermediate A solution of 10.0 grams (0.035 mole) of 4,6-diamino-1,2-dihydro-1-phenylmethoxy-2,2-dimethyl-1,3,5-triazine hydrochloride and 20 ml of water in 30 ml of ethanol was hydrogenated in the presence of 1.0 gram of 5% palladium on charcoal using a Parr hydrogenator. Upon completion of the uptake of the theoretical amount of hydrogen, the reaction mixture was filtered. The filtrate was concentrated under reduced pressure to a residual solid. The solid was recrystallized from ethanol, yielding 4.7 grams of 4,6-diamino-1,2-dihydro-1-hydroxy-2,2-dimethyl-1,3,5-triazine hydrochloride, m.p. 241° C. (dec.). The NMR spectrum was consistent with the proposed structure. The reaction was repeated several times to provide sufficient material for the next step.

Step D: Synthesis of 4,6-diamino-1,2-dihydro-1-hydroxy-2,2,-dimethyl-1,3,5-triazine as an intermediate This compound was prepared in a manner analogous to that of Example 2, using 47.9 grams (0.247 mole) of 4,6-diamino-1,2-dihydro-1-hydroxy-2,2-dimethyl-1,3,5-triazine hydrochloride in 100 ml of water and a 3.5 cm diameter column containing 350 ml of a strongly basic gel-type ion-exchange resin. An additional 500 ml of water was passed through the column to remove the maximum amount of product. The combined eluants were concentrated under reduced pressure, yielding 37.9 grams of 4,6-diamino-1,2-dihydro-1-hydroxy-2,2-dimethyl-1,3,5-triazine; m.p. 211°-212° C. (dec). The NMR spectrum was consistent with the proposed structure.

Step E: Synthesis of 2,4,5-trichlorophenylmethyl bromide as an intermediate

Under a nitrogen atmosphere, a stirred solution of 5.0 grams (0.026 mole) of 2,4,5-trichlorotoluene and 5.3 grams (0.030 mole) of N-bromosuccinimide in 30 ml of carbon tetrachloride was heated to reflux and then was irradiated with a sun lamp during a 10 minute period. The reaction mixture was allowed to cool to ambient temperature at which time it was filtered to remove excess succinimide. The filtrate was concentrated under reduced pressure to a residual oil. The oil was distilled under vacuum, yielding four fractions in the boiling point range of 130°-152° C./5 mm Hg. NMR analysis of the fractions indicated that two fractions, boiling point 140°-150° C./5 mm Hg., contained the majority of the reaction product. The two fractions were combined and diluted with 1 ml of petroleum ether. The mixture was filtered to remove unreacted starting material. The filtrate was diluted with 12 ml of petroleum ether, and the solution was cooled in dry-ice. The solvent was removed from the resultant solid by pipette. The solid was dried under reduced pressure, yielding 2.7 grams of 80% pure 2,4,5-trichlorophenylmethyl bromide. The NMR spectrum was consistent with the proposed structure.

Step F: Synthesis of 4,6-diamino-1,2-dihydro-1-(2,4,5-trichlorophenylmethoxy)-2,2-dimethyl-1,3,5-triazine hydrobromide (Compound 60)

A solution of 0.6 gram (0.004 mole) of 4,6-diamino-1,2-dihydro-1-hydroxy-2,2-dimethyl-1,3,5-triazine and 1.6 grams (0.006 mole) of 2,4,5-trichlorophenylmethyl bromide in 5 ml of dimethylformamide was stirred in a closed reaction vessel during about an 18 hour period. After this time the reaction mixture was concentrated under reduced pressure to a residual solid. The solid was washed with 50 ml of acetone. The dried solid was recrystallized from 125 ml of water, yielding 1.1 grams of 4,6-diamino-1,2-dihydro-1-(2,4,5-trichlorophenylmethoxy)-2,2-dimethyl-1,3,5-triazine hydrobromide, m.p. 247°-248° C. The NMR spectrum was consistent with the proposed structure.

EXAMPLE 4

SYNTHESIS OF 4,6-DIAMINO-1,2-DIHYDRO-2,2-DIMETHYL-1-[2-(NAPHTH-1-YL)ETHOXY]-1,3,5-TRIAZINE HYDROBROMIDE (COMPOUND 98)

This compound was prepared in a manner analogous to that of Example 3, Step F, using 0.8 gram (0.005 mole) of 4,6-diamino-1,2-dihydro-1-hydroxy-2,2-dimethyl-1,3,5-triazine (prepared in Example 3) and 1.3 grams (0.006 mole) of 2-(naphth-1-yl)ethyl bromide (commercially available) in 15 ml of dimethylformamide. The reaction product was recrystallized from water, yielding 0.4 gram of 4,6-diamino-1,2-dihydro-2,2-dimethyl-1-[2-(naphth-1-yl)ethoxy]-1,3,5-triazine hydrobromide. The NMR spectrum was consistent with the proposed structure.

EXAMPLE 5

SYNTHESIS OF 4,6-DIAMINO-2-ETHYL-1,2-DIHYDRO-2-METHYL-1-(NAPHTH-1-YLMETHOXY)-1,3,5-TRIAZINE HYDROCHLORIDE (COMPOUND 99)

This compound was prepared in a manner analogous to that of Example 1, Step E, using 1.0 gram (0.004 mole) of 1-(naphth-1-ylmethoxy)diguanide (prepared in Example 1, steps A-D), and 0.8 ml of concentrated hydrochloric acid in 20 ml of ethyl methyl ketone. The yield of 4,6-diamino-2-ethyl-1,2-dihydro-2-methyl-1-(naphth-1-ylmethoxy)-1,3,5-triazine hydrochloride was 0.9 gram; m.p. 206°–208° C. The NMR spectrum was consistent with the proposed structure.

EXAMPLE 6

SYNTHESIS OF 4,6-DIAMINO-1,2-DIHYDRO-2,2-DIMETHYL-1-[2,3-DIBROMO-3-(3,4-DICHLOROPHENYL)-PROPOXY]-1,3,5-TRIAZINE HYDROCHLORIDE (COMPOUND 16)

A stirred suspension of 0.8 gram (0.002 mole) of 4,6-diamino-1,2-dihydro-2,2-dimethyl-1-[3-(3,4-dichlorophenyl)prop-2-enoxy]-1,3,5-triazine hydrochloride (Compound 20 - prepared in a manner analogous to that of Example 3) in 10 ml of acetic acid was cooled in an ice-water bath. The reaction vessel was covered with aluminum foil to maintain darkness, and then 0.1 ml (0.002 mole) of bromine in 10 ml of acetic acid was added dropwise. Upon completion of addition, the reaction mixture was stirred about 1 hour until the bromine color had disappeared. The reaction mixture was then concentrated under reduced pressure to a residue. The residue was stirred in 25 ml of boiling water containing 1 ml of aqueous 6N hydrochloric acid. The mixture was cooled, and a solid was collected by filtration. The solid was dried, yielding 0.5 gram of 4,6-diamino-1,2-dihydro-2,2-dimethyl-1-[2,3-dibromo-3-(3,4-dichlorophenyl)propoxy]-1,3,5-triazine hydrochloride. The NMR spectrum was consistent with the proposed structure.

EXAMPLE 7

SYNTHESIS OF 4,6-DI(FURAN-2-YLCARBONYLAMINO)-1,2-DIHYDRO-2,2-DIMETHYL-1-(NAPHTH-1-YLMETHOXY)-1,3,5-TRIAZINE (COMPOUND 106)

To a stirred mixture of 0.7 gram (0.002 mole) of 4,6-diamino-1,2-dihydro-2,2-dimethyl-1-(naphth-1-ylmethoxy)-1,3,5-triazine hydrochloride (prepared in a manner analogous to that of Example 1) and 0.9 gram (0.009 mole) of sodium carbonate in 30 ml of methylene chloride was added 0.6 gram (0.005 mole) of 2-furanoyl chloride, followed by 1 ml of triethylamine. Upon completion of addition, the reaction mixture was stirred for about 18 hours after which time it was concentrated under reduced pressure to a residue. The residue was taken up in 100 ml of ethyl acetate and 100 ml of water. An insoluble material was removed by filtration. The organic layer was washed with 500 ml of an aqueous solution saturated with sodium chloride. The organic layer was then dried with sodium sulfate and filtered through a layer of silica gel. The filtrate was concentrated under reduced pressure to a residue. This residue was stirred with a solution of 20 ml of diethyl ether and 0.5 ml of methylene chloride. The solid was collected by filtration and was washed with ethanol, yielding, when dried, 0.4 gram of 4,6-di(furan-2-ylcarbonylamino)-1,2-dihydro-2,2-dimethyl-1-(naphth-1-ylmethoxy)-1,3,5-triazine; m.p. 173°–177° C. The NMR spectrum was consistent with the proposed structure.

EXAMPLE 8

SYNTHESIS OF 4,6-DIAMINO-1,2-DIHYDRO-2,2-DIMETHYL-1-(2,4,5-TRICHLOROPHENYLMETHOXY)-1,3,5-TRIAZINE, PAMOIC ACID SALT (COMPOUND 146)

Step A Synthesis of 4,6-diamino-1,2-dihydro-2,2-dimethyl-1-(2,4,5-trichlorophenylmethoxy)-1,3,5-triazine as an intermediate A solution of 0.5 gram (0.001 mole) of 4,6-diamino-1,2-dihydro 2,2-dimethyl-1-(2,4,5-trichlorophenylmethoxy)-1,3,5-triazine hydrobromide (Compound 60 - Prepared in Example 3) in 30 ml of water was stirred and 1 ml (0.007 mole) of triethylamine was added. The resultant solid was collected by filtration and dried, yielding 0.4 gram of 4,6-diamino-1,2-dihydro-2,2-dimethyl-1-(2,4,5-trichlorophenylmethoxy)-1,3,5-triazine. The NMR spectrum was consistent with the proposed structure.

Step B Synthesis of 4,6-diamino-1,2-dihydro-2,2-dimethyl-1-(2,4,5-trichlorophenylmethoxy)-1,3,5-triazine, pamoic acid salt (Compound 146)

A solution of 0.4 gram (0.001 mole) of 4,6-diamino-1,2-dihydro-2,2-dimethyl-1-(2,4,5-trichlorophenylmethoxy)-1,3,5-triazine and 0.2 gram (0.0005 mole) of pamoic acid in 50 ml of tetrahydrofuran was stirred for about 15 minutes. The reaction mixture was concentrated under reduced pressure to a residual solid. The solid was dried under high vacuum, yielding 0.6 gram of 4,6-diamino-1,2-dihydro-2,2-dimethyl-1-(2,4,5-trichlorophenylmethoxy)-1,3,5-triazine, pamoic acid salt, m.p. 180° C., dec. The NMR spectrum was consistent with the proposed structure.

Appended TABLE 1 lists 229 species of triazines and salts thereof falling within Formula I (supra) of this invention, the preparation of certain of which species are illustrated in accordance with foregoing Examples 1–8. TABLE 1-a provides the melting point and emperical formula of the majority of these species.

TABLE 1

4,6-DIAMINO-1,2-DIHYDRO-1,3,5-TRIAZINE DERIVATIVES

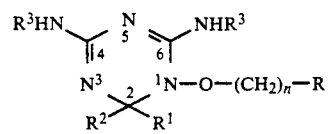

wherein $R^1$, $R^2$ are —$CH_3$ and $R^3$ is hydrogen:

| Compound Number | n | R | Salt |
|---|---|---|---|
| 1 | 1 | —$CH_3$ | HBr |
| 2 | 1 | —$C_2H_5$ | HCl |
| 3 | 1 | —$C_3H_7$ | HCl |
| 4 | 1 | —$C_5H_{11}$ | HBr |
| 5 | 1 | —$C_8H_{17}$ | HBr |
| 6 | 1 | —$C_8H_{17}$ | — |
| 7 | 1 | —$C_9H_{19}$ | HBr |
| 8 | 1 | —$C_{10}H_{21}$ | HBr |
| 9 | 1 | —$C_{11}H_{23}$ | HBr |
| 10 | 1 | —$C_{12}H_{25}$ | HBr |
| 11 | 1 | —$C_{13}H_{27}$ | HBr |
| 12 | 2 | —$CH(CH_3)_2$ | HBr |
| 13 | 1 | —$CH(C_2H_5)_2$ | HBr |
| 14 | 1 | Cyclopropyl | HBr |
| 15 | 1 | Cyclobutyl | HBr |
| 16 | 1 | 1,2-Dibromo-2-(3,4-dichlorophenyl)-ethyl | HCl |
| 17 | 1 | —CH=$CH_2$ | HBr |
| 18 | 2 | —CH=$CH_2$ | HBr |
| 19 | 1 | 2-Phenylethenyl | HBr |
| 20 | 1 | 2-(3,4-dichlorophenyl)ethenyl | HCl |
| 21 | 1 | —C≡CH | HBr |
| 22 | 3 | —C≡$CCH_3$ | HCl |
| 23 | 3 | —C≡$CC_2H_5$ | HCl |
| 24 | 3 | —C≡$CC_3H_7$ | HCl |
| 25 | 1 | 2-(3,4-Dichlorophenyl)ethynyl | HCl |
| 26 | 1 | —$CH_2F$ | HBr |
| 27 | 2 | —$OC_2H_5$ | HBr |
| 28 | 3 | —Oφ; 2,4,5-$Cl_3$ | HBr |
| 29 | 3 | —Oφ; 2,4,5-$Cl_3$ | — |
| 30 | 1 | —$CO_2CH_3$ | HBr |
| 31 | 2 | pyridin-2-yl | — |
| 32 | 2 | phthalimido | HBr |
| 33 | 3 | phthalimido | HBr |
| 34 | 1 | benzo[1,3]dioxol-5-yl | HBr |
| 35 | 1 | 2,2-dimethyl-2,3-dihydrobenzofuranyl | HBr |

TABLE 1-continued 4,6-DIAMINO-1,2-DIHYDRO-1,3,5-TRIAZINE DERIVATIVES

| 36 | 1 | (coumarin with OCH₃) | HBr |
| 37 | 1 | (coumarin with two OCH₃) | |

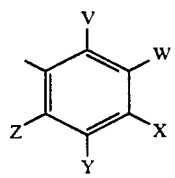

wherein $R^1$, $R^2$ are —CH₃; $R^3$ is hydrogen; and R is,

| Compound Number | n | V | W | X | Y | Z | Salt |
|---|---|---|---|---|---|---|---|
| 38 | 1 | H | H | H | H | H | HCl |
| 39 | 3 | H | H | H | H | H | HBr |
| 40 | 1 | Cl | H | H | H | H | HCl |
| 41 | 1 | H | Cl | H | H | H | HBr |
| 42 | 1 | H | H | Cl | H | H | HCl |
| 43 | 2 | H | H | Cl | H | H | HCl |
| 44 | 1 | F | H | H | H | H | HCl |
| 45 | 1 | H | H | F | H | H | HBr |
| 46 | 1 | Cl | Cl | H | H | H | HBr |
| 47 | 1 | Cl | H | Cl | H | H | HCl |
| 48 | 1 | Cl | H | H | Cl | H | HCl |
| 49 | 1 | Cl | H | H | Cl | H | HBr |
| 50 | 1 | Cl | H | H | H | Cl | HCl |
| 51 | 1 | H | Cl | Cl | H | H | HCl |
| 52 | 1 | H | Cl | Cl | H | H | — |
| 53 | 2 | H | Cl | Cl | H | H | HCl |
| 54 | 3 | H | Cl | Cl | H | H | HCl |
| 55 | 4 | H | Cl | Cl | H | H | HCl |
| 56 | 1 | H | Cl | H | Cl | H | HCl |
| 57 | 1 | F | H | H | H | F | HBr |
| 58 | 1 | Cl | Cl | H | Cl | H | HBr |
| 59 | 1 | H | Cl | Cl | Cl | H | HCl |
| 60 | 1 | Cl | H | Cl | Cl | H | HBr |
| 61 | 1 | Cl | H | Cl | Cl | H | — |
| 62 | 1 | F | H | F | H | F | HBr |
| 63 | 1 | Cl | H | Cl | Br | H | HBr |
| 64 | 1 | F | F | F | F | F | HBr |
| 65 | 1 | F | F | —CH₃ | F | F | HBr |
| 66 | 1 | Cl | H | Cl | φ | H | HBr |
| 67 | 1 | —CH₃ | H | H | H | —CH₃ | HBr |
| 68 | 1 | H | cyclohexyl | H | H | H | HI |
| 69 | 2 | H | H | —OCH₃ | H | H | HBr |
| 70 | 1 | H | —OC₇H₁₅ | H | H | H | HBr |
| 71 | 1 | H | —O(CH₂)₃φ | H | H | H | HBr |
| 72 | 1 | H | —NO₂ | H | H | H | HBr |
| 73 | 1 | H | H | —NO₂ | H | H | HBr |
| 74 | 1 | H | H | —CF₃ | H | H | HBr |
| 75 | 1 | H | —OCF₃ | H | H | H | HBr |
| 76 | 1 | H | —OCF₂CHF₂ | H | H | H | HCl |
| 77 | 1 | φ | H | H | H | H | HCl |
| 78 | 1 | H | φ | H | H | H | HBr |
| 79 | 1 | H | H | φ | H | H | HBr |
| 80 | 1 | —CH₃ | φ | H | H | H | HCl |
| 81 | 1 | —CH₃ | φ | H | H | —CH₃ | HBr |
| 82 | 1 | H | φ; 4-Cl | H | H | H | HBr |
| 83 | 1 | H | φ; 4-F | H | H | H | HBr |

TABLE 1-continued
4,6-DIAMINO-1,2-DIHYDRO-1,3,5-TRIAZINE DERIVATIVES

| | | | | | | | |
|---|---|---|---|---|---|---|---|
| 84 | 1 | H | φ | H | H | H | HCl |
| 85 | 1 | H | H | φ | H | H | HCl |
| 86 | 1 | H | φ | F | H | H | HBr |

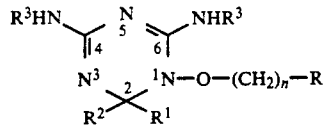

wherein R is

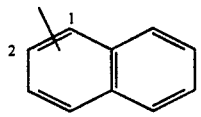

| Compound Number | n | R1 | R2 | R3 | Point of Attachment on Naphthyl | Salt |
|---|---|---|---|---|---|---|
| 87 | 1 | —CH₃ | H | H | 1 | HCl |
| 88 | 1 | —C₂H₅ | H | H | 1 | HCl |
| 89 | 1 | —CH₂CH₂φ | H | H | 1 | HCl |
| 90 | 1 | —CH=CHφ | H | H | 1 | HCl |
| | | | a Hydrate | | | |
| 91 | 1 | φ; 2-OCH₃ | H | H | 1 | 2HCl |
| | | | An isopropanol Complex | | | |
| 92 | 1 | —CH₃ | —CH₃ | H | 1 | HCl |
| 93 | 1 | —CH₃ | —CH₃ | H | 1 | Nonanoic Acid |
| 94 | 1 | —CH₃ | —CH₃ | H | 1 | Tetradecanoic Acid |
| 95 | 1 | —CH₃ | —CH₃ | H | 1 | — |
| 96 | 1 | —CH₃ | —CH₃ | H | 2 | HCl |
| 97 | 1 | —CH₃ | —CH₃ | H | 2 | — |
| 98 | 2 | —CH₃ | —CH₃ | H | 1 | HBr |
| 99 | 1 | —C₂H₅ | —CH₃ | H | 1 | HCl |
| 100 | 1 | —CH₂CH₂CH₂CH₂CH₂— | | H | 1 | HCl |
| 101 | 1 | —CH₃ | —CH₃ | —C(O)CH₃ | 1 | — |
| 102 | 1 | —CH₃ | —CH₃ | —C(O)C₂H₅ | 1 | — |
| 103 | 1 | —CH₃ | —CH₃ | —C(O)CH(CH₃)₂ | 1 | — |
| 104 | 1 | —CH₃ | —CH₃ | Cyclopropylcarbonyl | 1 | — |
| 105 | 1 | —CH₃ | —CH₃ | —C(O)CH₂OCH₃ | 1 | — |
| 106 | 1 | —CH₃ | —CH₃ | Furan-2-ylcarbonyl | 1 | — |

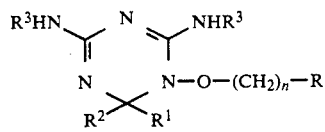

wherein R¹, R² are —CH₃ and R³ is hydrogen.

| Compound Number | n | R | Salt |
|---|---|---|---|
| 107 | 1 | H | HBr |
| 108 | 1 | C₆H₁₃ | HBr |
| 109 | 1 | C₇H₁₅ | HBr |
| 110 | 3 | CH(CH₃)₂ | HBr |
| 111 | 1 | Cyclohexyl | HBr |
| 112 | 1 | Cyclohex-3-ene | HBr |
| 113 | 1 | Cycloheptane | HBr |
| 114 | 1 | 1-(2-Fluorophenyl)-propan-2-yl | HBr |
| 115 | 1 | 1-(4-Methoxyphenyl)-propan-2-yl | HBr |
| 116 | 2 | 1-(4-Methoxyphenyl)-ethyl | HBr |
| 117 | 2 | (Cyclopropyl)(phenyl)-methyl | HBr |
| 118 | 1 | 2-(2,4,5-Trichloro-phenyl)ethenyl | HCl |
| 119 | 1 | 2-(2,5-dichloro-4-methylphenyl)ethenyl | HCl |
| 120 | 1 | 2-(2,5-Dibromo-4-methylphenyl)ethenyl | HCl |

TABLE 1-continued
4,6-DIAMINO-1,2-DIHYDRO-1,3,5-TRIAZINE DERIVATIVES

| | | | |
|---|---|---|---|
| 121 | 5 | CH₂Cl<br>70% Component of<br>Compound 123 | HBr |
| 122 | 5 | CH₂Br<br>30% Compound of<br>Compound 123 | HBr |
| 123 | A mixture of Compounds 121 and 122 | | HBr |
| 124 | 3 | Oφ;<br>2,4,6-Trimethyl | HBr |
| 125 | 2 | Naphth-1-yloxy | HBr |
| 126 | 2 | Naphth-2-yloxy | HBr |
| 127 | 1 | Sφ;<br>4-Cl | HCl |
| 128 | 1 | 5-Chlorothien-2-yl | HCl |
| 129 | 1 | phthalimido | HBr |
| 130 | 2 | 4,5-dichlorophthalimido | HBr |
| 131 | 3 | 4,5-dichlorophthalimido | HBr |
| 132 | 1 | 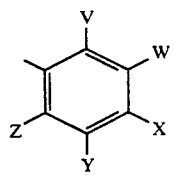 | HCl | wherein R¹, R² are —CH₃; R³ is hydrogen; and R is, (phenyl ring with substituents V, W, X, Y, Z)

| Compound Number | n | V | W | X | Y | Z | Salt |
|---|---|---|---|---|---|---|---|
| 133 | 1 | H | Br | H | H | H | HBr |
| 134 | 1 | H | I | H | H | H | HBr |
| 135 | 1 | H | H | I | H | H | HBr |
| 136 | 1 | CH₃ | H | H | H | H | HBr |
| 137 | 1 | H | H | OCH₃ | H | H | HBr |
| 138 | 1 | H | H | OC₂H₅ | H | H | HBr |
| 139 | 1 | H | H | OCF₃ | H | H | HBr |
| 140 | 1 | SCH₃ | H | H | H | H | HBr |
| 141 | 1 | F | H | Br | H | H | HBR |
| 142 | 1 | Cl | H | H | Br | H | HBR |
| 143 | 1 | F | H | H | Br | H | HBr |
| 144 | 3 | Cl | H | H | H | Cl | HBr |
| 145 | 1 | H | Br | F | H | H | HBr |
| 146 | 1 | Cl | H | Cl | Cl | H | Pamoic* acid |
| 147 | 1 | Cl | H | Cl | Br | H | Pamoic* acid |
| 148 | 1 | Cl | H | CH₃ | Cl | H | HBr |
| 149 | 1 | Br | H | CH₃ | Br | H | HBr |
| 150 | 1 | Cl | H | Cl | CH₃ | H | HBr |

TABLE 1-continued
4,6-DIAMINO-1,2-DIHYDRO-1,3,5-TRIAZINE DERIVATIVES

| | | | | | | | |
|---|---|---|---|---|---|---|---|
| 151 | 3 | Cl | H | Cl | Cl | H | HCl |
| 152 | 1 | Cl | H | Cl | H | Cl | HCl |
| 153 | 3 | Cl | H | CH₃ | Cl | H | HCl |
| 154 | 3 | Br | H | CH₃ | Br | H | HCl |
| 155 | 1 | Cl | H | Cl | OCH₃ | H | HBr |
| 156 | 3 | H | φ | H | H | H | HBr |
| 157 | 1 | H | φ | H | H | H | Pamoic* acid |
| 158 | 1 | H | φ; 3,4-Cl₂ | H | H | H | HBr |
| 159 | 1 | F | φ | H | H | H | HBr |
| 160 | 1 | H | φ | F | H | H | HBr |
| 161 | 1 | H | φ 4-F | F | H | H | HBr |
| 162 | 1 | Cl | H | H | φ | H | HBr |
| 163 | 1 | F | H | H | φ | H | HBr |
| 164 | 1 | F | φ | F | H | H | HBr | wherein R is

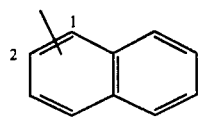

| Compound Number | n | R1 | R2 | R3 | Point of Attachment on Naphthyl | Salt |
|---|---|---|---|---|---|---|
| 165 | 1 | CH₃ | CH₃ | H | 1 | Butyric acid |
| 166 | 1 | CH₃ | CH₃ | H | 1 | Pentanoic acid |
| 167 | 1 | CH₃ | CH₃ | H | 1 | Hexanoic acid |
| 168 | 1 | CH₃ | CH₃ | H | 1 | D-gluconic* acid |
| 169 | 1 | CH₃ | CH₃ | H | 1 | Barbituric* acid |

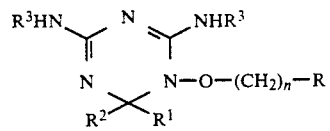

wherein R¹, R² are —CH₃ and R³ is hydrogen.

| Compound Number | n | R | Salt |
|---|---|---|---|
| 170 | 2 | —C(CH₃)₃ | HBr |
| 171 | 1 | 3-Phenylcyclohexyl 15% trans-85% cis | HBr |
| 172 | 1 | 3-(2-Methylphenyl)-cyclohexyl 5% trans-95% cis | — |
| 173 | 1 | 3-(3-Methylphenyl)-cyclohexyl 100% cis | HBr |
| 174 | 1 | 3-(4-Methylphenyl)-cyclohexyl 5% trans-95% cis | HBr |
| 175 | 1 | 3-(4-Methylphenyl) cyclohexyl 70% trans-30% cis | HBr |
| 176 | 1 | 1-Phenylpropan-2-yl | HBr |
| 177 | 1 | 1-(3-Bromophenyl)-propan-2-yl | HBr |
| 178 | 2 | 1-Phenylethyl | HBr |
| 179 | 2 | (Cyclopropyl)(4-fluorophenyl)methyl | HBr |
| 180 | 2 | (Cyclopropyl)(4-methoxyphenyl)methyl | HBr |
| 181 | 1 | 2-(5-Bromo-2,4-dichlorophenyl)ethenyl | HCl |
| 182 | 1 | 2-(4-Bromo,2,5-dichlorophenyl)ethenyl | HCl |
| 183 | 1 | 2-(2-Bromo-4,5-dichlorophenyl)ethenyl | HCl |
| 184 | 2 | Oφ; 4-Cl | HBr |

TABLE 1-continued
4,6-DIAMINO-1,2-DIHYDRO-1,3,5-TRIAZINE DERIVATIVES

| | | | |
|---|---|---|---|
| 185 | 2 | Oφ; 4-Br | HCl |
| 186 | 3 | Oφ | HBr |
| 187 | 3 | Oφ; 2-CH₃ | HBr |
| 188 | 3 | Oφ; 3-CH₃ | HBr |
| 189 | 3 | Oφ; 4-CH₃ | HBr |
| 190 | 3 | Oφ; 2,3-(CH₃)₂ | HBr |
| 191 | 3 | Oφ; 2,4-(CH₃)₂ | HBr |
| 192 | 3 | Oφ; 2,5-(CH₃)₂ | HBr |
| 193 | 3 | Oφ; 2,6-(CH₃)₂ | HBr |
| 194 | 3 | Oφ; 3,4-(CH₃)₂ | HBr |
| 195 | 3 | Oφ; 3,5-(CH₃)₂ | HBr |
| 196 | 3 | Oφ; 2,3,5-(CH₃)₃ | HBr |
| 197 | 3 | Oφ; 3,4,5-(CH₃)₃ | HBr |
| 198 | 2 | Oφ; 2,3,6-(CH₃)₃ | HBr |
| 199 | 2 | Sφ | HCl |
| 200 | 2 | Sφ; 4-Cl | — |
| 201 | 2 | Adamant-l-yl | HBr |
| 202 | 1 | Benzo[b]thien-2-yl | HBr |
| 203 | 3 | 2,2-Dimethyl-benzofuran-7-yloxy | HBr | wherein $R^1$, $R^2$ are —CH₃; $R^3$ is hydrogen; and R is:

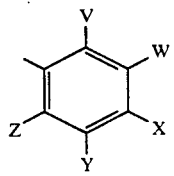

| Compound | n | V | W | X | Y | Z | Salt |
|---|---|---|---|---|---|---|---|
| 204 | 3 | H | H | Cl | H | H | HCl |
| 205 | 1 | H | H | Br | H | H | HBr |
| 206 | 1 | H | F | H | H | H | HBr |
| 207 | 1 | H | —CF₃ | H | H | H | HBr |
| 208 | 1 | H | —CN | H | H | H | HBr |
| 209 | 1 | H | H | —CN | H | H | HBr |
| 210 | 3 | H | H | —OCF₃ | H | H | HBr |
| 211 | 1 | H | F | F | H | H | HBr |
| 212 | 1 | Cl | H | H | NO₂ | H | HBr |
| 213 | 1 | Cl | H | Cl | Br | H | — |
| 214 | 1 | Cl | H | Cl | Br | H | *Sulfamethoxypyridazine |
| 215 | 3 | Cl | H | Cl | Br | H | HCl |
| 216 | 3 | Cl | H | Br | Cl | H | HCl |
| 217 | 3 | Br | H | Cl | Cl | H | HCl |
| 218 | 1 | —CH₃ | H | —CH₃ | —CH₃ | H | HBr |
| 219 | 3 | H | H | —OCH₃ | H | H | HBr |
| 220 | 3 | —OCH₃ | H | —OCH₃ | —OCH₃ | H | HBr |
| 221 | 1 | H | φ; 2-Cl | H | H | H | HBr |
| 222 | 1 | H | φ; 3-Cl | H | H | H | HBr |
| 223 | 1 | H | φ; 4-OCF₃ | H | H | H | HBr |
| 224 | 3 | Cl | H | H | φ | H | HBr |
| 225 | 1 | F | H | H | φ; 4-F | H | HBr |
| 226 | 1 | F | H | H | φ; 2,6-F₂ | H | HBr |
| 227 | 1 | F | φ; | F | H | H | HBr | wherein $R^1$ and $R^2$ are —CH₃; $R^3$ is hydrogen; and R, in which V and W, taken together, form an aryl ring, is

TABLE 1-continued
4,6-DIAMINO-1,2-DIHYDRO-1,3,5-TRIAZINE DERIVATIVES

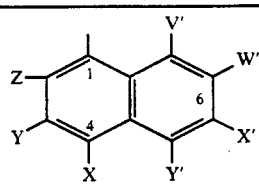

| Compound | n | X | Y | Z | V' | W' | X' | Y' | Salt |
|---|---|---|---|---|---|---|---|---|---|
| 228 | 1 | Cl | H | H | H | H | H | H | HBr |
| 229 | 1 | H | H | H | H | H | Br | H | HBr |

Pamoic Acid

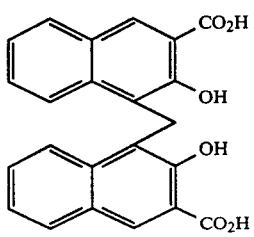

D-gluconic Acid

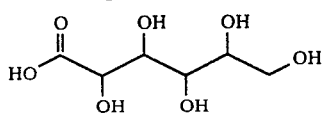

Barbituric Acid

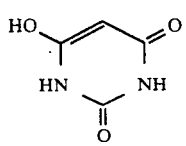

Sulfamethoxypyridazine

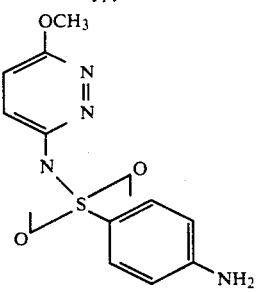

TABLE 1-a

| Compound Number | Melting Point (°C.) | Empirical Formula |
|---|---|---|
| 1 | 197–200 | $C_7H_{16}BrN_5O$ |
| 2 | 206–208 | $C_8H_{18}ClN_5O$ |
| 3 | 204–206 | $C_9H_{20}ClN_5O$ |
| 4 | 204–207 | $C_{11}H_{24}BrN_5O$ |
| 5 | 196–197 | $C_{14}H_{30}BrN_5O$ |
| 6 | 148–149 | $C_{14}H_{29}N_5O$ |
| 7 | 195–196 | $C_{15}H_{32}BrN_5O$ |
| 8 | 195–197 | $C_{16}H_{34}BrN_5O$ |
| 9 | 199–200 | $C_{17}H_{36}BrN_5O$ |
| 10 | 199–200 | $C_{18}H_{38}BrN_5O$ |
| 11 | 199–200 | $C_{19}H_{40}BrN_5O$ |
| 12 | 206–209 | $C_{10}H_{22}BrN_5O$ |
| 13 | — | $C_{11}H_{24}BrN_5O$ |
| 14 | 205–207 | $C_9H_{18}BrN_5O$ |
| 15 | 212–215 | $C_{10}H_{20}BrN_5O$ |
| 16 | 209–211 | $C_{14}H_{18}Br_2Cl_3N_5O$ |
| 17 | 193–195 | $C_8H_{16}BrN_5O$ |
| 18 | 218–220 | $C_9H_{18}BrN_5O$ |
| 19 | 216–218 | $C_{14}H_{20}BrN_5O$ |
| 20 | 231–232 | $C_{14}H_{18}Cl_3N_5O$ |
| 21 | 198–200 | $C_8H_{14}BrN_5O$ |
| 22 | 200–202 | $C_{11}H_{20}ClN_5O$ |
| 23 | 194–198 | $C_{12}H_{22}ClN_5O$ |
| 24 | 208–212 | $C_{13}H_{24}ClN_5O$ |
| 25 | 210–211 | $C_{14}H_{16}Cl_3N_5O$ |
| 26 | 215–217 | $C_7H_{15}BrFN_5O$ |
| 27 | 202–204 | $C_9H_{20}BrN_5O_2$ |
| 28 | 191–193 | $C_{14}H_{19}BrCl_3N_5O_2$ |
| 29 | 209–211 | $C_{14}H_{18}Cl_3N_5O_2$ |
| 30 | 145–149 | $C_8H_{16}BrN_5O_3$ |
| 31 | 218, dec. | $C_{12}H_{18}N_6O$ |
| 32 | 216–219 | $C_{15}H_{19}BrN_6O_3$ |
| 33 | 200–202 | $C_{16}H_{21}BrN_6O_3$ |
| 34 | 210–212 | $C_{13}H_{18}BrN_5O_3$ |

TABLE 1-a-continued

| Compound Number | Melting Point (°C.) | Empirical Formula |
|---|---|---|
| 35 | 187-190 | $C_{16}H_{24}BrN_5O_2$ |
| 36 | 226-228 | $C_{16}H_{20}BrN_5O_4$ |
| 37 | 227-230 | $C_{17}H_{22}BrN_5O_5$ |
| 38 | 218-219 | $C_{12}H_{18}ClN_5O$ |
| 39 | — | $C_{14}H_{22}BrN_5O$ |
| 40 | 213-214 | $C_{12}H_{17}Cl_2N_5O$ |
| 41 | 241-242 | $C_{12}H_{17}BrClN_5O$ |
| 42 | 241-242 | $C_{12}H_{17}Cl_2N_5O$ |
| 43 | 230-232 | $C_{13}H_{19}Cl_2N_5O$ |
| 44 | 223-225 | $C_{12}H_{17}ClFN_5O$ |
| 45 | 218-220 | $C_{12}H_{17}BrFN_5O$ |
| 46 | 209-212 | $C_{12}H_{16}BrCl_2N_5O$ |
| 47 | 219-220 | $C_{12}H_{16}Cl_3N_5O$ |
| 48 | 236-238 | $C_{12}H_{16}Cl_3N_5O$ |
| 49 | 211-213 | $C_{12}H_{16}BrCl_2N_5O$ |
| 50 | 232-233 | $C_{12}H_{16}Cl_3N_5O$ |
| 51 | 234-235 | $C_{12}H_{16}Cl_3N_5O$ |
| 52 | 169-170, remelts at 224 | $C_{12}H_{15}Cl_2N_5O$ |
| 53 | 249-250 | $C_{13}H_{18}Cl_3N_5O$ |
| 54 | 231-232 | $C_{14}H_{20}Cl_3N_5O$ |
| 55 | 218-219 | $C_{15}H_{22}Cl_3N_5O$ |
| 56 | 231-233 | $C_{12}H_{16}Cl_3N_5O$ |
| 57 | 226-228 | $C_{12}H_{16}BrF_2N_5O$ |
| 58 | — | $C_{12}H_{15}BrCl_3N_5O$ |
| 59 | 233-234 | $C_{12}H_{15}Cl_4N_5O$ |
| 60 | 247-248 | $C_{12}H_{15}BrCl_3N_5O$ |
| 61 | 200, dec., remelts at 245 | $C_{12}H_{14}Cl_3N_5O$ |
| 62 | 214-217 | $C_{12}H_{15}BrF_3N_5O$ |
| 63 | 244-245 | $C_{12}H_{15}Br_2Cl_2N_5O$ |
| 64 | 216-218 | $C_{12}H_{13}BrF_5N_5O$ |
| 65 | 220-222 | $C_{13}H_{16}BrF_4N_5O$ |
| 66 | 160. dec. | $C_{18}H_{20}BrClN_5O$ |
| 67 | 214-216 | $C_{14}H_{22}BrN_5O$ |
| 68 | 207-209 | $C_{18}H_{30}IN_5O$ |
| 69 | 213-216 | $C_{14}H_{22}BrN_5O_2$ |
| 70 | 165-168 | $C_{19}H_{32}BrN_5O_2$ |
| 71 | 182-185 | $C_{21}H_{28}BrN_5O_2$ |
| 72 | 236-238 | $C_{12}H_{17}BrN_6O_3$ |
| 73 | 233-235 | $C_{12}H_{17}BrN_6O_3$ |
| 74 | 223-225 | $C_{13}H_{17}BrF_3N_5O$ |
| 75 | 202-204 | $C_{13}H_{17}BrF_3N_5O_2$ |
| 76 | 208-216 | $C_{14}H_{18}BrF_4N_5O_2$ |
| 77 | 221-222 | $C_{18}H_{22}ClN_5O$ |
| 78 | 213-215 | $C_{18}H_{22}BrN_5O$ |
| 79 | 233-236 | $C_{18}H_{22}BrN_5O$ |
| 80 | 211-213 | $C_{19}H_{24}ClN_5O$ |
| 81 | 215-217 | $C_{20}H_{26}BrN_5O$ |
| 82 | 222-225 | $C_{18}H_{21}BrClN_5O$ |
| 83 | 225-228 | $C_{18}H_{21}BrFN_5O$ |
| 84 | 200-203 | $C_{18}H_{22}ClN_5O_2$ |
| 85 | 224-226 | $C_{18}H_{22}ClN_5O_2$ |
| 86 | 216-219 | $C_{18}H_{21}BrFN_5O_2$ |
| 87 | 219-224 | $C_{15}H_{18}ClN_5O$ |
| 88 | 150 | $C_{16}H_{20}ClN_5O$ |
| 89 | 152 | $C_{22}H_{24}ClN_5O$ |
| 90 | 232-234 | $C_{22}H_{24}ClN_5O$ |
| 91 | 201-203 | $C_{24}H_{31}Cl_2N_5O_3$ |
| 92 | 217-218 | $C_{16}H_{20}ClN_5O$ |
| 93 | Paste | $C_{25}H_{37}N_5O_3$ |
| 94 | 178-186 | $C_{30}H_{47}N_5O_3$ |
| 95 | 170-171 | $C_{16}H_{19}N_5O$ |
| 96 | 234-235 | $C_{18}H_{20}ClN_5O$ |
| 97 | 169-170, remelts at 244 | $C_{16}H_{19}N_5O$ |
| 98 | — | $C_{17}H_{22}BrN_5O$ |
| 99 | 206-208 | $C_{17}H_{22}ClN_5O$ |
| 100 | 216-218 | $C_{19}H_{24}ClN_5O$ |
| 101 | 152-154 | $C_{20}H_{23}N_5O_3$ |
| 102 | 164-166 | $C_{22}H_{27}N_5O_3$ |
| 103 | 169-171 | $C_{24}H_{31}N_5O_3$ |
| 104 | 183-184 | $C_{24}H_{27}N_5O_3$ |
| 105 | 137-138 | $C_{22}H_{27}N_5O_5$ |
| 106 | 173-177 | $C_{26}H_{23}N_5O_5$ |
| 107 | 178-180 | $C_6H_{14}BrN_5O$ |
| 108 | 192-194 | $C_{12}H_{26}BrN_5O$ |
| 109 | 196-197 | $C_{13}H_{28}BrN_5O$ |
| 110 | 217-219 | $C_{11}H_{24}BrN_5O$ |
| 111 | 229-231 | $C_{12}H_{24}BrN_5O$ |
| 112 | 232-234 | $C_{12}H_{22}BrN_5O$ |
| 113 | 220-222 | $C_{13}H_{26}BrN_5O$ |
| 114 | 188-191 | $C_{15}H_{23}BrFN_5O$ |
| 115 | 213-216 | $C_{16}H_{26}BrN_5O$ |
| 116 | 201-203 | $C_{16}H_{26}BrN_5O$ |
| 117 | 218-221 | $C_{17}H_{26}BrN_5O$ |
| 118 | 249-250 | $C_{14}H_{17}Cl_4N_5O$ |
| 119 | 225-227 | $C_{15}H_{20}Cl_3N_5O$ |
| 120 | 222-223 | $C_{15}H_{20}Br_2ClN_5O$ |
| 121 | 196-198 | $C_{11}H_{23}BrClN_5O$ |
| 122 | 196-198 | $C_{11}H_{23}Br_2N_5O$ |
| 123 | 196-198 | $C_{22}H_{46}Br_3ClN_{10}O_2$ |
| 124 | 215-217 | $C_{17}H_{28}BrN_5O_2$ |
| 125 | 190-193 | $C_{17}H_{22}BrN_5O_2$ |
| 126 | 201-204 | $C_{17}H_{22}BrN_5O_2$ |
| 127 | 198-200 | $C_{12}H_{17}Cl_2N_5OS$ |
| 128 | 224-226 | $C_{10}H_{15}Cl_2N_5OS$ |
| 129 | 220-222 | $C_{14}H_{17}BrN_6O_5$ |
| 130 | 192-195 | $C_{15}H_{17}BrCl_2N_6O_3$ |
| 131 | 210-213 | $C_{16}H_{19}BrCl_2N_6O_3$ |
| 132 | 231-232 | $C_{13}H_{17}Cl_2N_5O_3$ |
| 133 | 227-229 | $C_{12}H_{17}Br_2N_5O$ |
| 134 | 232-235 | $C_{12}H_{17}BrIN_5$ |
| 135 | 228-231 | $C_{12}H_{17}BrIN_5$ |
| 136 | 212-214 | $C_{13}H_{20}BrN_5O$ |
| 137 | 215-217 | $C_{13}H_{20}ClN_5O_2$ |
| 138 | 215-217 | $C_{14}H_{22}BrN_5O_2$ |
| 139 | 220-222 | $C_{13}H_{17}BrF_3N_5O_2$ |
| 140 | 213-216 | $C_{13}H_{20}BrN_5OS$ |
| 141 | 218-220 | $C_{12}H_{16}Br_2FN_5O$ |
| 142 | 218-220 | $C_{12}H_{16}Br_2ClN_5O$ |
| 143 | 237-240 | $C_{12}H_{16}Br_2FN_5O$ |
| 144 | 205-207 | $C_{14}H_{20}BrCl_2N_5O$ |
| 145 | 218-220 | $C_{12}H_{16}Br_2FN_5O$ |
| 146 | 180, dec. | $C_{47}H_{44}Cl_{16}N_{10}O_8$ |
| 147 | Gum | $C_{47}H_{44}Br_2Cl_{14}N_{10}O_8$ |
| 148 | 238-241 | $C_{13}H_{18}BrCl_2N_5O$ |
| 149 | 238-240 | $C_{13}H_{18}Br_3N_5O$ |
| 150 | 230-231 | $C_{13}H_{18}BrCl_2N_5O$ |
| 151 | 230-231 | $C_{14}H_{19}Cl_4N_5O$ |
| 152 | 232-233 | $C_{12}H_{15}Cl_4N_5O$ |
| 153 | 222-223 | $C_{15}H_{22}Cl_3N_5O$ |
| 154 | 220-221 | $C_{15}H_{22}Br_2ClN_5O$ |
| 155 | 215-216 | $C_{13}H_{18}BrCl_2N_5O_2$ |
| 156 | 208-210 | $C_{20}H_{26}BrN_5O$ |
| 157 | Gum | $C_{59}H_{58}N_{10}O_8$ |
| 158 | 225-227 | $C_{18}H_{20}BrCl_2N_5O$ |
| 159 | 225-227 | $C_{18}H_{21}BrFN_5O$ |
| 160 | 212-214 | $C_{18}H_{21}BrFN_5O$ |
| 161 | 220-223 | $C_{18}H_{20}BrF_2N_5O$ |
| 162 | 221-224 | $C_{18}H_{21}BrClN_5O$ |
| 163 | 226-228 | $C_{18}H_{21}BrFN_5O$ |
| 164 | 223-225 | $C_{18}H_{20}BrF_2N_5O$ |
| 165 | 167-170 | $C_{20}H_{27}N_5O_3$ |
| 166 | Paste | $C_{21}H_{29}N_5O_3$ |
| 167 | Paste | $C_{22}H_{31}N_5O_3$ |
| 168 | Paste | $C_{22}H_{31}N_5O_3$ |
| 169 | 202, dec. | $C_{20}H_{23}N_7O_4$ |
| 170 | 220-222 | $C_{11}H_{24}BrN_5O$ |
| 171 | 218-220 dec. | $C_{18}H_{28}BrN_5O$ |
| 172 | 100 | $C_{19}H_{29}N_5O$ |
| 173 | 231-232 | $C_{19}H_{30}BrN_5O$ |
| 174 | 241-242 dec. | $C_{19}H_{30}BrN_5O$ |
| 175 | 228-229 dec. | $C_{19}H_{30}BrN_5O$ |
| 176 | 192-197 | $C_{15}H_{24}BrN_5O$ |
| 177 | 208-211 | $C_{15}H_{23}Br_2N_5O$ |
| 178 | 187-188 | $C_{15}H_{24}BrN_5O$ |
| 179 | 223-224 | $C_{17}H_{25}BrFN_5O$ |
| 180 | 221-222 | $C_{18}H_{28}BrN_5O$ |
| 181 | 234-235 | $C_{14}H_{17}BrCl_3N_5O$ |
| 182 | 242-243 dec. | $C_{14}H_{17}BrCl_3N_5O$ |
| 183 | 236-237 | $C_{14}H_{17}BrCl_3N_5O$ |
| 184 | 205-207 | $C_{13}H_{19}BrClN_5O_2$ |
| 185 | 202-205 | $C_{13}H_{19}BrClN_5O_2$ |
| 186 | 205-207 | $C_{14}H_{22}BrN_5O_2$ |
| 187 | 205 | $C_{15}H_{24}BrN_5O_2$ |

TABLE 1-a-continued

| Compound Number | Melting Point (°C.) | Empirical Formula |
|---|---|---|
| 188 | 209 | $C_{15}H_{24}BrN_5O_2$ |
| 189 | 223 | $C_{15}H_{24}BrN_5O_2$ |
| 190 | 214–215 | $C_{16}H_{26}BrN_5O_2$ |
| 191 | 211 | $C_{16}H_{26}BrN_5O_2$ |
| 192 | 210 | $C_{16}H_{26}BrN_5O_2$ |
| 193 | 240–242 | $C_{16}H_{26}BrN_5O_2$ |
| 194 | 214–215 | $C_{16}H_{26}BrN_5O_2$ |
| 195 | 205 | $C_{16}H_{26}BrN_5O_2$ |
| 196 | 212 | $C_{17}H_{28}BrN_5O_2$ |
| 197 | 205 | $C_{17}H_{28}BrN_5O_2$ |
| 198 | 210–212 | $C_{17}H_{28}BrN_5O_2$ |
| 199 | 198–200 | $C_{13}H_{20}ClN_5OS$ |
| 200 | 197–200 | $C_{13}H_{18}ClN_5OS$ |
| 201 | 226–227 | $C_{17}H_{30}BrN_5O$ |
| 202 | 223–225 | $C_{14}H_{28}BrN_5OS$ |
| 203 | 184–185 | $C_{18}H_{28}BrN_5O_3$ |
| 204 | 221–223 | $C_{14}H_{21}Cl_2N_5O$ |
| 205 | 215–217 | $C_{12}H_{17}Br_2N_5O$ |
| 206 | 221–223 | $C_{12}H_{17}BrFN_5O$ |
| 207 | 212–214 | $C_{13}H_{17}BrF_3N_5O$ |
| 208 | 235–237 | $C_{13}H_{17}BrN_6O$ |
| 209 | 233–236 | $C_{13}H_{17}BrN_6O$ |
| 210 | 207–209 | $C_{15}H_{21}BrF_3N_5O_2$ |
| 211 | 212–216 | $C_{12}H_{16}BrF_2N_5O$ |
| 212 | 239–240 | $C_{12}H_{16}BrClN_6O_3$ |
| 213 | 233–234 | $C_{12}H_{14}BrCl_2N_5O$ |
| 214 | 161–168 | $C_{23}H_{26}BrCl_2N_9O_4S$ |
| 215 | 233–234 | $C_{14}H_{19}BrCl_3N_5O$ |
| 216 | 229–230 | $C_{14}H_{19}BrCl_3N_5O$ |
| 217 | 219–220 | $C_{14}H_{19}BrCl_3N_5O$ |
| 218 | 225–227 | $C_{15}H_{24}BrN_5O$ |
| 219 | 209–212 | $C_{15}H_{24}BrN_5O_2$ |
| 220 | 210–211 | $C_{17}H_{28}BrN_5O_4$ |
| 221 | 216–217 | $C_{18}H_{21}BrClN_5O$ |
| 222 | 210–213 | $C_{18}H_{21}BrClN_5O$ |
| 223 | 213–214 | $C_{19}H_{21}BrF_3N_5O_2$ |
| 224 | 206–208 | $C_{20}H_{25}BrClN_5O$ |
| 225 | 237–238 | $C_{18}H_{20}BrF_2N_5O$ |
| 226 | 220–222 | $C_{18}H_{19}BrF_3N_5O$ |
| 227 | 233–235 | $C_{18}H_{19}BrF_3N_5O$ |
| 228 | — | $C_{16}H_{19}BrClN_5O$ |
| 229 | — | $C_{16}H_{19}Br_2N_5O$ |

Insecticide Formulations

In the normal use of the insecticidal triazines of the present invention, the triazines usually will not be employed free from admixture or dilution, but ordinarily will be used in a suitable formulated composition compatible with the method of application and comprising an insecticidally effective amount of the triazine. The triazines of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present triazines may be applied, for example, as sprays, dusts, or granules to the area where pest control is desired, the type of application varying of course with the pest and the environment. Thus, the triazines of this invention may be formulated as granules of large particle size, as powdery dusts, as wettable powders, as emulsifiable concentrates, as solutions, and the like. It will be understood that the insecticides themselves may be present as essentially pure compounds, or as mixtures of these triazine compounds.

Granules may comprise porous or nonporous particles, such as attapulgite clay or sand, for example, which serve as carriers for the triazines. The granule particles are relatively large, a diameter of about 400–2500 microns typically. The particles are either impregnated with the triazine from solution or coated with the triazine, adhesive sometimes being employed. Granules generally contain 0.05–10%, preferably 0.5–5%, active ingredient as the insecticidally effective amount.

Dusts are admixtures of the triazines with finely divided solids such as talc, attapulgite clay, kieselguhr, pyrophyllite, chalk, diatomaceous earths, calcium phosphates, calcium and magnesium carbonates, sulfur, flours, and other organic and inorganic solids which acts carriers for the insecticide. These finely divided solids have an average particle size of less than about 50 microns. A typical dust formulation useful for controlling insects contains 1 part of triazine, such as 4,6-diamino-1,2-dihydro-2,2-dimethyl-1-(3,4-dichlorophenylmethoxy)-1,3,5-triazine (Compound 2), and 99 parts of talc.

The triazines of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5–50% triazine, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects contains 1.5 parts each of sodium lignosulfonate and sodium lauryl sulfate as wetting agents, 25 parts of Compound 52 (above), and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the triazines with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylaryl sulfonates, including fatty methyl taurides; alkylaryl polyether alcohols, sulfates of higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1-15% by weight of the insecticidal composition.

Other useful formulations include simple solutions of the active ingredient in a solvent in which it is completely soluble at the desired concentrations, such as acetone or other organic solvents.

An insecticidally effective amount of triazine in an insecticidal composition diluted for application is normally in the range of about 0.001% to about 8% by weight. Many variations of spraying and dusting compositions known in the art may be used by substituting the triazines of this invention into compositions known or apparent in the art.

The insecticidal compositions of this invention may be formulated with other active ingredients, including other insecticides, nematicides, acaricides, fungicides, plant growth regulators, fertilizers, etc. In using the compositions to control insects, it is only necessary that an insecticidally effective amount of triazine be applied to the locus where control is desired. Such locus may, e.g., be the insects themselves, plants upon which the insects feed, or the insect habitat. When the locus is the soil, e.g., soil in which agricultural crops are or will be planted, the active compound may be applied to and optionally incorporated into the soil. For most applications, an insecticidally effective amount will be about 75 to 4000 g per hectare, preferably 150 g to 3000 g per hectare.

In both the solid and liquid formulations described above, it has been found that the addition of an ultraviolet light (u.v.) stabilizer to the formulations is particularly useful and advantageous in prolonging the activity, i.e., the photostability, of the compounds of this invention when they are exposed to light or photosensitizers on the leaves of the sprayed plants. Thus, for example, the addition of 2-hydroxy-4-n-octoxybenzophenone in photostabilizing amounts to the insecticidal formulation of Compound 78 (above) can reduce the photolysis rate of the triazines several-fold when tested in artificial sunlight. In particular, it has been found that the addition of from about 0.02 to 2.0 parts by weight of the above octoxybenzophenone per part by weight of the triazine composition, is effective for this purpose.

Biological Data

Representative compounds of the present invention were tested in the laboratory as aqueous acetone or aqueous methanol solutions containing a small amount of octylphenoxypolyethoxyethanol surfactant. The insecticidal activity of these compounds against the tobacco budworm is summarized in TABLE 2 (below).

Compounds 60 and 78 were also formulated as 10% wettable powder formulations. A typical 10% wettable powder formulation consists of the following:

| Wettable Powder, 10% | Percent by Weight |
| --- | --- |
| Active ingredient (95%) | 10.5 |
| Dispersing Agent | 4.0 |
| Wetting Agent | 1.0 |
| Carrier/Diluent | 84.5 |
| | 100.00 |

The dispersing agent was sugar free, sodium based sulfonates of Kraft lignin sold under the trademark "Polyfon F". (Westvaco Polychemical Corp., Charleston Heights, S.C.) The wetting agent was sodium alkylnaphthalene sulfonate sold under the trademark "Nekal BX-78". (Rhone Poulenc, Dayton, N.J.) The carrier/diluent was an attapulgite clay.

The 4,6-diamino-1,2-dihydro-1,3,5-triazine derivatives of the present invention were tested for insecticidal activity in foliar evaluations against the tobacco budworm (*Heliothis virescens* [Fabricius]).

In these tests against the tobacco budworm, nine-day-old chickpea plants (*Cicer arietinum*) were sprayed at 20 psi to runoff on both upper and lower leaf surfaces with solutions of test chemical to provide application rates as high as 3000 ppm of active ingredient. The solvent used to prepare the solutions of the test chemical was 10% acetone or methanol (v/v), and 0.1% of the surfactant, octylphenoxypolyethoxyethanol in distilled water. Four replicates, each containing four chickpea plants, for each rate of application of test chemical were sprayed. The treated plants were transferred to a hood where they were kept until the spray had dried.

The four chickpea plants in each replicate treated with test chemical as described above were removed from their pots by cutting the stems just above the soil line. The excised leaves and stems from the four plants in each replicate were placed in individual 8-ounce paper cups. Five first-instar (4-5 days old) tobacco budworms were counted into each cup, taking care not to cause injury. An opaque plastic lid was placed on each cup which was then held in a growth chamber for a 96 hour exposure period at 25° C. and 50% relative humidity. At the end of the 96 hour exposure period the cups were opened, and the numbers of dead and live insects were counted. Moribund larvae which were disoriented or unable to crawl normally were counted as dead. Using the insect counts, the efficacy of the test chemical was expressed in percent mortality. The condition of test plant was also observed for phytotoxicity and for reduction of feeding damage as compared to an untreated check.

In an alternate test method, 10% wettable powder formulations of Compounds 146, 147, and 157 were tested against tobacco budworm on chickpea plants and cabbage looper on pinto bean (*Phaseolus vulgaris*) plants. The candidate insecticides were applied as aqueous solutions of the 10% wettable powder formulations at rates o application equivalent to 1.0 pound active ingredient/acre (lb/A) and submultiples thereof, for example 0.5 lb/A, 0.25 lb/A, and so on. In these tests, nine-day-old test plants were sprayed with the test chemical solutions at a delivery rate of 30 gallons/acre at 40 psi with the nozzle of the spray machine adjusted to 10.5 inches above the foliage of the test plants. Four replicates each containing four plants for each rate of application of test chemical, were sprayed.

The aqueous test chemical solutions were prepared by dissolving 1.2 grams of the 10% wettable powder formulation in 30 ml of distilled water. For the 1.0 lb/A rate of application, 15 ml of the solution was sprayed onto the test plants as described above. The remaining 15 ml of test solution was diluted with 15 ml of distilled water. A 15 ml aliquot of the resultant solution was removed and sprayed onto test plants to provide a rate of application of 0.5 lb/A. The serial dilution and spraying was continued to provide the appropriate lower rates of application.

Upon completion of spraying the remaining portion of the test was conducted as described above with the 4-5 day-old tobacco budworm.

These tested compounds (Compounds 146, 147, and 157) were likewise generally very active against the tobacco budworm. The results of these alternate tests are also reported in TABLE 2 below.

Selected compounds of the present invention were also tested by the foliar spraying methods of compounds 1 et seq. of TABLE 2 (other than the wettable powder) against other insect species, which included fall armyworm (*Spodoctera frugiperda* [J. E. Smith]), imported cabbageworm (*Pieris rapae* [Linnaeus]), Mexican bean beetle (*Epilachna varivestis* Mulsant), southern armyworm (*Spodoptera eridania* [Cramer]), soybean looper (*Pseudoplusia includens* [Walker], beet armyworm (*Spodoptera exigua* [Hubner]), corn earworm (*Heliothis zea* [Boddie]), cabbage looper (*Trichoplusia ni* [Hubner]), diamondback moth (*Pluttela xylostella* [Linnaeus]), European corn borer (*Ostrinia nubilalis* [Hubner]), and black cutworm (*Agrotis ipsilon* [Hufnagel]). The insecticidal activity against these species is summarized in TABLE 3 below.

The compounds of the present invention appear to be especially suited for use on cole crops, sweet corn, tobacco, and cotton against foliar-feeding lepidoptera.

TABLE 2

RESULTS OF FOLIAR SPRAY EVALUATIONS* AGAINST SELECTED SPECIES OF THE ORDER LEPIDOPTERA (TOBACCO BUDWORM - TBW)

| Cmpd No. | Rate (PPM) | % KILL |
|---|---|---|
| 1 | 30 | 90 |
|   | 10 | 19 |
| 2 | 300 | 33 |
|   | 30 | 0 |
| 3 | 300 | 85 |
|   | 30 | 0 |
| 4 | 30 | 70 |
|   | 10 | 11 |
| 5 | 30 | 72 |
|   | 10 | 25 |
| 6 | 30 | 84 |
|   | 10 | 85 |
| 7 | 30 | 67 |
|   | 10 | 13 |
| 8 | 30 | 81 |
|   | 10 | 0 |
| 9 | 30 | 42 |
|   | 10 | 11 |
| 10 | 30 | 13 |
|   | 10 | 12 |
| 11 | 30 | 6 |
|   | 10 | 0 |
| 12 | 30 | 60 |
|   | 10 | 0 |
| 13 | 10 | 85 |
|   | 3 | 11 |
| 14 | 300 | 44 |
|   | 30 | 0 |
| 15 | 30 | 75 |
|   | 10 | 28 |
| 16 | 300 | 95 |
|   | 30 | 47 |
| 17 | 300 | 17 |
|   | 30 | 6 |
| 18 | 300 | 70 |
|   | 30 | 0 |
| 19 | 300 | 33 |
|   | 30 | 10 |
| 20 | 300 | 44 |
|   | 30 | 13 |
| 21 | 300 | 5 |
|   | 30 | 42 |
| 22 | 300 | 0 |
| 23 | 300 | 95 |
|   | 30 | 38 |
| 24 | 30 | 63 |
|   | 10 | 0 |
| 25 | 300 | 0 |
| 26 | 300 | 0 |
| 27 | 300 | 0 |
| 28 | 30 | 79 |
|   | 10 | 55 |
| 29 | 30 | 75 |
|   | 10 | 60 |
| 30 | 300 | 0 |
| 31 | 300 | 89 |
|   | 30 | 37 |
| 32 | 30 | 90 |
|   | 10 | 6 |
| 33 | 30 | 85 |
|   | 10 | 40 |
| 34 | 300 | 90 |
|   | 30 | 17 |
| 35 | 300 | 6 |
|   | 30 | 6 |
| 36 | 300 | 10 |
|   | 30 | 0 |
| 37 | 30 | 42 |
|   | 10 | 11 |
| 38 | 300 | 39 |
|   | 100 | 15 |
| 39 | 300 | 0 |
| 40 | 300 | 90 |
|   | 100 | 70 |
| 41 | 30 | 31 |
|   | 10 | 38 |
| 42 | 100 | 70 |
|   | 30 | 70 |
| 43 | 3 | 65 |
|   | 1 | 0 |
| 44 | 30 | 44 |
|   | 10 | 50 |
| 45 | 300 | 70 |
|   | 30 | 0 |
| 46 | 300 | 89 |
|   | 30 | 5 |
| 47 | 64 | 60 |
|   | 32 | 70 |
| 48 | 30 | 29 |
|   | 10 | 42 |
| 49 | 300 | 90 |
|   | 30 | 18 |
| 50 | 1000 | 50 |
|   | 300 | 0 |
| 51 | 100 | 90 |
|   | 54 | 82 |
| 52 | 32 | 93 |
|   | 17 | 73 |
| 53 | 10 | 80 |
|   | 3 | 21 |
| 54 | 30 | 95 |
|   | 10 | 85 |
| 55 | 30 | 50 |
|   | 10 | 0 |
| 56 | 30 | 25 |
|   | 10 | 0 |
| 57 | 3000 | 84 |
|   | 1000 | 33 |
| 58 | 30 | 60 |
|   | 10 | 13 |
| 59 | 30 | 75 |
|   | 10 | 20 |
| 60 | 3 | 72 |
|   | 1 | 6 |
| 61 | 30 | 85 |
|   | 10 | 25 |
| 62 | 3000 | 65 |
|   | 1000 | 31 |
| 63 | 3 | 70 |
|   | 1 | 53 |
| 64 | 3000 | 30 |
|   | 1000 | 6 |
| 65 | 1000 | 79 |
|   | 540 | 65 |

TABLE 2-continued

RESULTS OF FOLIAR SPRAY EVALUATIONS* AGAINST SELECTED SPECIES OF THE ORDER LEPIDOPTERA (TOBACCO BUDWORM - TBW)

| Cmpd No. | Rate (PPM) | % KILL |
|---|---|---|
| 66 | 30 | 95 |
|  | 10 | 60 |
| 67 | 3000 | 36 |
|  | 1000 | 5 |
| 68 | 30 | 29 |
|  | 10 | 0 |
| 69 | 10 | 61 |
|  | 6.4 | 100 |
| 70 | 300 | 90 |
|  | 30 | 5 |
| 71 | 300 | 85 |
|  | 30 | 0 |
| 72 | 300 | 90 |
|  | 100 | 70 |
| 73 | 300 | 90 |
|  | 30 | 11 |
| 74 | 300 | 45 |
|  | 30 | 0 |
| 75 | 30 | 0 |
| 76 | 30 | 0 |
| 77 | 300 | 11 |
|  | 30 | 0 |
| 78 | 30 | 95 |
|  | 10 | 65 |
| 79 | 300 | 85 |
|  | 30 | 0 |
| 80 | 300 | 90 |
|  | 30 | 6 |
| 81 | 3000 | 78 |
|  | 1000 | 25 |
| 82 | 30 | 95 |
|  | 10 | 24 |
| 83 | 30 | 89 |
|  | 10 | 72 |
| 84 | 30 | 31 |
|  | 10 | 0 |
| 85 | 1000 | 75 |
|  | 540 | 85 |
| 86 | 300 | 95 |
|  | 30 | 12 |
| 87 | 300 | 5 |
|  | 30 | 5 |
| 88 | 300 | 0 |
| 89 | 300 | 0 |
| 90 | 300 | 0 |
| 91 | 300 | 5 |
|  | 30 | 0 |
| 92 | 30 | 95 |
|  | 10 | 71 |
| 93 | 30 | 72 |
|  | 10 | 6 |
| 94 | 30 | 20 |
|  | 10 | 0 |
| 95 | 32 | 93 |
|  | 17 | 80 |
| 96 | 30 | 95 |
|  | 10 | 75 |
| 97 | 32 | 93 |
|  | 17 | 87 |
| 98 | 3 | 75 |
|  | 1 | 10 |
| 99 | 300 | 95 |
|  | 30 | 50 |
| 100 | 300 | 5 |
|  | 30 | 11 |
| 101 | 30 | 65 |
|  | 10 | 5 |
| 102 | 30 | 47 |
|  | 10 | 10 |
| 103 | 30 | 47 |
|  | 10 | 0 |
| 104 | 300 | 95 |
|  | 30 | 30 |
| 105 | 30 | 45 |
|  | 10 | 0 |
| 106 | 30 | 60 |
| 107 | 10 | 0 |
|  | 300 | 56 |
|  | 30 | 18 |
| 108 | 30 | 95 |
|  | 10 | 67 |
| 109 | 30 | 50 |
|  | 10 | 12 |
| 110 | 30 | 26 |
|  | 10 | 0 |
| 111 | 30 | 95 |
|  | 10 | 53 |
| 112 | 30 | 90 |
|  | 10 | 75 |
| 113 | 10 | 95 |
|  | 3 | 21 |
| 114 | 30 | 95 |
|  | 10 | 85 |
| 115 | 300 | 95 |
|  | 30 | 80 |
| 116 | 30 | 95 |
|  | 10 | 90 |
| 117 | 30 | 95 |
|  | 10 | 75 |
| 118 | 640 | 80 |
|  | 320 | 65 |
| 119 | 300 | 15 |
|  | 30 | 0 |
| 120 | 300 | 70 |
|  | 30 | 0 |
| 121 | No Data |  |
| 122 | No Data |  |
| 123 | 300 | 95 |
|  | 30 | 47 |
| 124 | 3 | 44 |
|  | 1 | 0 |
| 125 | 300 | 95 |
|  | 30 | 79 |
| 126 | 300 | 90 |
|  | 100 | 90 |
| 127 | 10 | 90 |
|  | 3 | 65 |
| 128 | 300 | 90 |
|  | 100 | 85 |
| 129 | 300 | 68 |
|  | 30 | 74 |
| 130 | 5000 | 0 |
| 131 | 300 | 80 |
|  | 30 | 35 |
| 132 | 100 | 95 |
|  | 30 | 80 |
| 133 | 170 | 80 |
|  | 100 | 58 |
| 134 | 100 | 72 |
|  | 30 | 42 |
| 135 | 30 | 85 |
|  | 10 | 25 |
| 136 | 300 | 85 |
|  | 100 | 45 |
| 137 | 300 | 95 |
|  | 100 | 33 |
| 138 | 1000 | 95 |
|  | 300 | 65 |
| 139 | 300 | 95 |
|  | 100 | 75 |
| 140 | 300 | 95 |
|  | 100 | 75 |
| 141 | 100 | 95 |
|  | 30 | 58 |
| 142 | 30 | 33 |
|  | 10 | 13 |
| 143 | 100 | 80 |
|  | 30 | 47 |
| 144 | 10 | 95 |
|  | 3 | 75 |
| 145 | 100 | 95 |
|  | 30 | 59 |

TABLE 2-continued
RESULTS OF FOLIAR SPRAY EVALUATIONS* AGAINST SELECTED SPECIES OF THE ORDER LEPIDOPTERA (TOBACCO BUDWORM - TBW)

| Cmpd No. | Rate (PPM) | % KILL |
|---|---|---|
| 146 | 1** | 100 |
| 147 | 1** | 100 |
| 148 | 30 | 95 |
|  | 10 | 55 |
| 149 | 30 | 67 |
|  | 10 | 32 |
| 150 | 30 | 95 |
|  | 10 | 80 |
| 151 | 30 | 95 |
|  | 10 | 47 |
| 152 | 1000 | 10 |
|  | 300 | 0 |
| 153 | 10 | 95 |
|  | 3 | 35 |
| 154 | 30 | 95 |
|  | 10 | 90 |
| 156 | 30 | 70 |
|  | 10 | 6 |
| 157 | 1** | 100 |
| 158 | 30 | 75 |
|  | 10 | 16 |
| 159 | 30 | 95 |
|  | 10 | 55 |
| 160 | 30 | 95 |
|  | 10 | 85 |
| 161 | 30 | 90 |
|  | 10 | 45 |
| 162 | 30 | 80 |
|  | 10 | 50 |
| 163 | 30 | 89 |
|  | 10 | 17 |
| 164 | 30 | 95 |
|  | 10 | 65 |
| 165 | 300 | 95 |
|  | 30 | 65 |
| 166 | 30 | 90 |
|  | 10 | 75 |
| 167 | 30 | 75 |
|  | 10 | 53 |
| 168 | 30 | 55 |
|  | 10 | 22 |
| 169 | No Data |  |
| 170 | No Data |  |
| 171 | 100 | 94 |
|  | 30 | 83 |
| 172 | 100 | 95 |
|  | 30 | 65 |
| 173 | 100 | 95 |
|  | 30 | 70 |
| 174 | 100 | 90 |
|  | 30 | 69 |
| 175 | 100 | 65 |
|  | 30 | 55 |
| 176 | 30 | 95 |
|  | 10 | 90 |
| 177 | 30 | 95 |
|  | 10 | 89 |
| 178 | 30 | 95 |
|  | 10 | 50 |
| 179 | 100 | 95 |
|  | 30 | 85 |
| 180 | 30 | 80 |
|  | 10 | 21 |
| 181 | 300 | 16 |
|  | 100 | 6 |
| 182 | 300 | 33 |
|  | 100 | 6 |
| 183 | 300 | 53 |
|  | 100 | 5 |
| 184 | 100 | 80 |
|  | 30 | 15 |
| 185 | 300 | 95 |
|  | 100 | 55 |
| 186 | 30 | 95 |
|  | 10 | 55 |
| 187 | 100 | 95 |
|  | 30 | 95 |
| 188 | 300 | 95 |
|  | 100 | 89 |
| 189 | 30 | 83 |
|  | 10 | 61 |
| 190 | 10 | 95 |
|  | 3 | 70 |
| 191 | 3 | 75 |
|  | 1 | 21 |
| 192 | 10 | 94 |
|  | 3 | 72 |
| 193 | 30 | 84 |
|  | 10 | 74 |
| 194 | 30 | 95 |
|  | 10 | 78 |
| 195 | 30 | 95 |
|  | 10 | 85 |
| 196 | 10 | 95 |
|  | 3 | 84 |
| 197 | 100 | 95 |
|  | 30 | 74 |
| 198 | 100 | 95 |
|  | 30 | 95 |
| 199 | 30 | 83 |
|  | 10 | 40 |
| 200 | 100 | 89 |
|  | 30 | 89 |
| 201 | 30 | 95 |
|  | 10 | 100 |
| 202 | 100 | 95 |
|  | 30 | 55 |
| 203 | 300 | 90 |
|  | 100 | 50 |
| 204 | 30 | 95 |
|  | 10 | 90 |
| 205 | 100 | 90 |
|  | 30 | 85 |
| 206 | 300 | 85 |
|  | 100 | 50 |
| 207 | 100 | 75 |
|  | 30 | 35 |
| 208 | 100 | 95 |
|  | 30 | 95 |
| 209 | 100 | 63 |
|  | 30 | 15 |
| 210 | 300 | 94 |
|  | 100 | 94 |
| 211 | 300 | 90 |
|  | 100 | 47 |
| 212 | 100 | 85 |
|  | 30 | 15 |
| 213 | 100 | 87 |
|  | 30 | 94 |
| 214 | 30 | 94 |
|  | 10 | 82 |
| 215 | 30 | 95 |
|  | 10 | 56 |
| 216 | 10 | 80 |
|  | 3 | 30 |
| 217 | 30 | 95 |
|  | 10 | 85 |
| 218 | 300 | 95 |
|  | 100 | 95 |
| 219 | 30 | 95 |
|  | 10 | 50 |
| 220 | 100 | 95 |
|  | 30 | 80 |
| 221 | 30 | 95 |
|  | 10 | 60 |
| 222 | 100 | 95 |
|  | 30 | 75 |
| 223 | 100 | 95 |
|  | 30 | 70 |
| 224 | 100 | 95 |
|  | 30 | 53 |
| 225 | 100 | 90 |

TABLE 2-continued
RESULTS OF FOLIAR SPRAY EVALUATIONS* AGAINST SELECTED SPECIES OF THE ORDER LEPIDOPTERA (TOBACCO BUDWORM - TBW)

| Cmpd No. | Rate (PPM) | % KILL |
|---|---|---|
|  | 30 | 45 |
| 226 | 30 | 90 |
|  | 10 | 21 |
| 227 | 100 | 95 |
|  | 30 | 90 |

*Exposure time - 96 hrs
**Cmpds 146, 147, 157 - indicates data for a compound formulated as a 10% wettable powder.
Cmpds 146, 147, 157 - indicates rate units are in lbs/acre

TABLE 3
RESULTS OF FOLIAR SPRAY EVALUATIONS AGAINST SELECTED SPECIES OF THE ORDER *LEPIDOPTERA* AND *COLEOPTERA*

| COMPOUND NO. | *FAW | ICW | MBB | SAW | SBL | BAW | CEW | CL | DBM | ECB | BCW |
|---|---|---|---|---|---|---|---|---|---|---|---|
| 6 | | | | | | 5 | | 50 | | | |
| 13 | | | | | | 50 | 90 | 70 | | | |
| 28 | | 20 | 100 | | | 55 | 80 | 100 | | | |
| 29 | | | | | | | | 90 | | | |
| 30 | | | 5 | | | | | 85 | | | |
| 42 | | | | | | 45 | 50 | 30 | | | |
| 50 | | | | 40 | | | | | | | |
| 51 | | | | | $18^1$ | 95 | | | | | |
| 52 | 65 | | 45 | | | | 95 | 90 | | | |
| 53 | 70 | 95 | 90 | 65 | | 60 | 85 | 95 | | | |
| 59 | $100^2$ | 70 | 5 | 20 | | 95 | 90 | 90 | | | |
| 63 | $90^2$ | 30 | 70 | | | 50 | 85 | 65 | | | |
| 66 | | | 100 | | | 50 | 40 | 30 | | | |
| 69 | | | $5^3$ | | | | 50 | 85 | | | |
| 72 | | | | | | | | 50 | | | |
| 78 | $55^2$ | 95 | 100 | | | 70 | 65 | 90 | | | |
| 92 | 95 | | $25^3$ | 10 | $1^{4**}$ | 6 | $13^1$ | $40^5$ | 70 | 44 | 0 |
| 95 | | | . | | $19^1$ | 100 | | | | | |
| 96 | 100 | | 5 | 50 | | 33 | $56^1$ | $30^5$ | 75 | 44 | 0 |
| 97 | | | | | $18^1$ | 100 | | | | | |
| 98 | $85^2$ | | $70^2$ | 35 | | 85 | 100 | 65 | | | |
| 107 | | | | 0 | | | | | | | |
| 108 | 65 | | 10 | | | 35 | 40 | 65 | | | |
| 111 | 60 | | | | | | | | | | |
| 112 | | | | | | 25 | | 70 | | | |
| 123 | | | | | | $65^3$ | | | | | |
| 127 | | | | | | 40 | | 55 | | | |
| 128 | 40 | | | | | | | 25 | | | |
| 134 | | | | | | | | 90 | | | |
| 135 | 65 | | | | | | | | | | |
| 139 | | | | | | 70 | | 30 | | | |
| 144 | | | | | | 5 | | 37 | | | |
| 146 | | | | | | 15 | | 95 | | | |
| 147 | | | | | | $100^6$ | | $100^6$ | | | |
| 150 | | | | | | $100^6$ | | $100^6$ | | | |
| 152 | | | | | | 35 | | 90 | | | |
| 153 | 70 | | 100 | 95 | | 0 | | | | | |
| 154 | 75 | | 100 | 95 | | 70 | 90 | 45 | | | |
| 155 | | | | | | $35^3$ | | 15 | | | |
| 157 | | | | | | $100^6$ | | $100^6$ | | | |
| 162 | | | | | | 35 | | | | | |
| 177 | | | | | | $10^3$ | | 95 | | | |
| 186 | | | | | | 11 | | | | | |
| 190 | | | | | | 72 | | | | | |
| 193 | | | | | | 11 | | | | | |
| 194 | | | | | | 32 | | | | | |
| 199 | | | | | | 10 | | | | | |
| 200 | | | | | | 10 | | | | | |
| 204 | | | | | | 15 | | 90 | | | |
| 205 | | | | | | 25 | | 11 | | | |
| 210 | | | | | | 6 | | | | | |
| 212 | | | | | | $25^3$ | | | | | |
| 214 | | | | | | 30 | | | | | |
| 215 | | | | | | 5 | | 95 | | | |
| 216 | | | | | | 6 | | | | | |
| 218 | | | | | | $25^3$ | | | | | |
| 219 | | | | | | 19 | | | | | |
| 221 | | | | | | 71 | | | | | |
| 222 | | | | | | 80 | | | | | |
| 226 | | | | | | 25 | | | | | |

TABLE 3-continued
RESULTS OF FOLIAR SPRAY EVALUATIONS AGAINST SELECTED SPECIES OF THE ORDER *LEPIDOPTERA* AND *COLEOPTERA*

| | Percent Kill at 100 ppm | | | | | | | | | |
|---|---|---|---|---|---|---|---|---|---|---|
| COMPOUND NO. | *FAW | ICW | MBB | SAW | SBL | BAW | CEW | CL | DBM | ECB | BCW |
| 227 | | | | | 5 | | | | | | |

*FAW - fall armyworm
ICW - imported cabbage worm
MBB - Mexican bean beetle
SAW - southern armyworm
SBL - soybean looper
BAW - beet armyworm
CEW - corn earworm
CL - cabbage looper
DBM - diamondback moth
ECB - European corn borer
BCW - black cutworm
**I - Inactive
[1]at 32 ppm
[2]at 30 ppm
[3]at 1000 ppm
[4]at 15 ppm
[5]at 10 ppm
[6]at 0.5 lbs/acre

We claim:

1. An insecticidal composition comprising an insecticidal amount of the compound

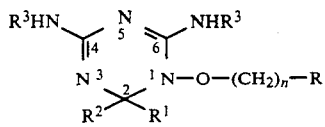

wherein R is selected from the group consisting of hydrogen, straight or branched chain alkyl, haloalkyl, (substituted aryl)haloalkyl, arylakyl, (substituted aryl)alkyl, (α-cycloalkyl)arylalkyl, cycloalkyl, arylcycloalkyl, (substituted aryl)cycloalkyl, alkenyl, cycloalkenyl, arylalkenyl, (substituted aryl)alkenyl, alkynyl, arylalkynyl, (substituted aryl)alkynyl, alkoxy, (substituted aryl)alkoxy, aryl, aryloxy, (substituted aryl)oxy, arylthio, (substituted aryl)thio, heterocyclclyl, alkoxycarbonyl, and substituted phenyl of the structure

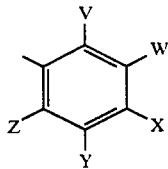

wherein
V, W, X, Y, and Z are independently selected from the group consisting of hydrogen, halogen, lower alkyl, haloalkyl, cycloalkyl, arylalkyl, alkoxy, haloalkoxy, arylalkoxy, aryl, substituted aryl, aryloxy, (substituted aryl)oxy, alkylthio, alkylsulfoxy, alkylsulfonyl, cyano, and nitro;
or V and W, or W and X, when taken together, comprise the ring-forming group

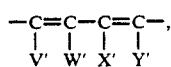

wherein V', W', X' and Y' have the same definition as V, W, X, and Y;
n is 1 to 5;

$R^1$ is selected from the group consisting of lower alkyl, arylalkyl, arylalkenyl, and alkoxyaryl;
or $R^2$ is selected from the group consisting of hydrogen and lower alkyl,
$R^1$ and $R^2$ taken together form a spirocycloalkane ring of 3 to 9 carbon atoms;
$R^3$ is selected from the group consisting of hydrogen, lower alkylcarbonyl, cyclopropylcarbonyl, methoxymethylcarbonyl, and 2-furanylcarbonyl;
and agriculturally acceptable salts thereof, in admixture with a compatible agricultural vehicle, wherein each alkyl, alkenyl, and alkynyl group independently contains up to 13 carbon atoms; the cycloalkyl groups contain 3 to 7 carbon atoms; and each aryl group is independently selected from the group consisting of phenyl, naphthyl, or phenanthryl which optionally substituted by one or more alkyl, halo, alkoxy, cycloalkyl, aryl, haloalkyl, haloalkoxy, cyano, nitro, dialkylamino or thioalkyl groups, and
wherein the heterocyclyl groups are selected from the group consisting of thienyl, furyl, pyranyl, triazinyl, pyrrlyl, imidazolyl, pyridyl, pyridazinyl, isoxazolyl, benzothienyl, isobenzofuranyl, indolyl, quinolyl, phthalimido, benzodioxolyl, benzodioxanyl, benzofuranyl, and benzopyranyl.

2. The composition of claim 1 wherein R is cycloalkyl, aryl, substituted phenoxy, substituted phenylthio, or substituted phenyl of the structure

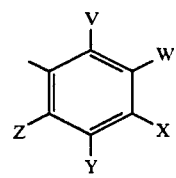

wherein
V, W, X, Y, and Z are independently halogen, or alkoxy, wherein at least one of V to Z is not hydrogen;
n is 1 to 4;
$R^1$ is methyl or ethyl;
$R^2$ is methyl;
$R^3$ is hydrogen;
or the acid salts thereof.

3. The composition of claim 1 wherein the insecticidal compound is 4,6-diamino-1,2-dihydro-2,2-dimethyl-1-(cycloheptylmethoxy)-1,3,5-triazine hydrobromide.

4. The composition of claim 1 wherein the insecticidal compound is 4,6-diamino-1,2-dihydro-2,2-dimethyl-1-[3-(4-methoxyphenyl)butoxy]-1,3,5-triazine hydrobromide.

5. The composition of claim 1 wherein the insecticidal compound is 4,6-diamino-1,2-dihydro-2,2-dimethyl-1-[3-(2,4,6-trimethylphenoxy)propoxy]-1,3,5-triazine hydrobromide.

6. The composition of claim 1 wherein the insecticidal compound is 4,6-diamino-1,2-dihydro-2,2-dimethyl-1-(4-chlorophenylthiomethoxy)-1,3,5-triazine hydrochloride.

7. The composition of claim 1 wherein the insecticidal compound is 4,6-diamino-1,2-dihydro-2,2-dimethyl-1-[3-(2,6-dichlorophenyl)propoxy]-1,3,5-triazine hydrobromide.

8. The composition of claim 1 wherein the insecticidal compound is 4,6-diamino-1,2-dihydro-2,2-dimethyl-1-(2,4,5-trichlorophenylmethoxy)-1,3,5-triazine, pamoic acid salt.

9. The composition of claim 1 wherein the insecticidal compound is 4,6-diamino-1,2-dihydro-2,2-dimethyl-1-(5-bromo-2,4-dichlorophenylmethoxy)-1,3,5-triazine, pamoic acid salt.

10. The composition of claim 1 wherein the insecticidal compound is 4,6-diamino-1,2-dihydro-2,2-dimethyl-1-(naphth-1-ylmethoxy)-1,3,5-triazine, pentanoic acid salt.

11. The composition of claim 1 wherein the insecticidal compound is 4,6-diamino-1,2-dihydro-2,2-dimethyl-1-[3-(2,4-dimethylphenoxy)propoxy]-1,3,5-triazine hydrobromide.

12. The composition of claim 1 wherein the insecticidal compound is 4,6-diamino-1,2-dihydro-2,2-dimethyl-1-[3-(2,5-dimethylphenoxy)propoxy]-1,3,5-triazine hydrobromide.

13. The composition of claim 1 wherein the insecticidal compound is 4,6-diamino-1,2-dihydro-2,2-dimethyl-1-[3-(2,3,5-trimethylphenoxy)propoxy]-1,3,5-triazine hydrobromide.

14. The composition of claim 1 wherein the insecticidal compound is 4,6-diamino-1,2-dihydro-2,2-dimethyl-1-[2-(adamant-1-yl)ethoxy]-1,3,5-triazine hydrobromide.

15. The composition of claim 1 wherein the insecticidal compound is 4,6-diamino-1,2-dihydro-2,2-dimethyl-1-(4-bromophenylmethoxy)-1,3,5-triazine hydrobromide.

16. The composition of claim 1 wherein the insecticidal compound is 4,6-diamino-1,2-dihydro-2,2-dimethyl-1-[3-(2-bromo-4,5-dichlorophenyl)propoxy]-1,3,5-triazine hydrochloride.

17. A method for controlling insects which comprises applying to the locus where control is desired an insecticidal amount of a compound of the formula

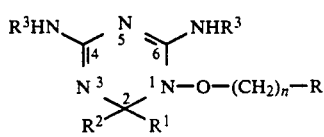

where R is selected from the group consisting of hydrogen, straight or branched chain alkyl, haloalkyl, (substituted aryl)haloalkyl, arylakyl, (substituted aryl)alkyl, (α-cycloalkyl)arylalkyl, cycloalkyl, arylcycloalkyl, (substituted aryl)cycloalkyl, alkenyl, cycloalkenyl, arylalkenyl, (substituted aryl)alkenyl, alkynyl, arylalkynyl, (substituted aryl)alkynyl, alkoxy, (substituted aryl)alkoxy, aryl, aryloxy, (substituted aryl)oxy, arylthio, (substituted aryl)thio, heterocyclclyl, alkoxycarbonyl, and substituted phenyl of the structure

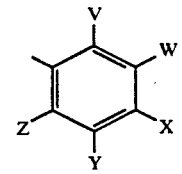

wherein
V, W, X, Y, and Z are independently selected from the group consisting of hydrogen, halogen, lower alkyl, haloalkyl, cycloalkyl, arylalkyl, alkoxy, haloalkoxy, arylalkoxy, aryl, substituted aryl, aryloxy, (substituted aryl)oxy, alkylthio, alkylsulfoxy, alkylsulfonyl, cyano, and nitro;
or V and W, or W and X, when taken together, comprise the ring-forming group

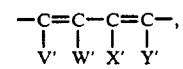

wherein V', W', X' and Y' have the same definition as V, W, X, and Y;
n is 1 to 5;
$R^1$ is selected from the group consisting of lower alkyl, arylalkyl, arylalkenyl, and alkoxyaryl;
$R^2$ is selected from the group consisting of hydrogen and lower alkyl;
or $R^1$ and $R^2$ taken together form a spirocycloalkane ring of 3 to 9 carbon atoms;
$R^3$ is selected from the group consisting of hydrogen, lower alkylcarbonyl, cyclopropylcarbonyl, methoxymethylcarbonyl, and 2-furanylcarbonyl;
and agriculturally acceptable salts thereof, in admixture with a compatible agricultural vehicle, wherein each alkyl, alkenyl, and alkynyl group independently contains up to 13 carbon atoms; the cycloalkyl groups contain 3 to 7 carbon atoms; and each aryl group is independently selected from the group consisting of phenyl, naphthyl, or phenanthryl which optionally are substituted by one or more alkyl, halo, alkoxy, cycloalkyl, aryl, haloalkyl, haloalkoxy, cyano, nitro, dialkylamino or thioalkyl groups, and
wherein the heterocyclyl groups are selected from the group consisting of thienyl, furyl, pyranyl, triazinyl, pyrrlyl, imidazolyl, pyridyl, pyridazinyl, isoxazolyl, benzothienyl, isobenzofuranyl, indolyl, quinolyl, phthalimido, benzodioxolyl, benzodioxanyl, benzofuranyl, and benzopyranyl.

18. The method of claim 17 wherein R is cycloalkyl, aryl, substituted phenoxy, substituted phenylthio, or substituted phenyl of the structure

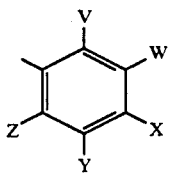

wherein
V, W, X, Y, and Z are independently halogen or alkoxy, wherein at least one of V to Z is not hydrogen;
n is 1 to 4;
$R^1$ is methyl or ethyl;
$R^2$ is methyl
$R^3$ is hydrogen;
or the acid salts thereof.

19. The method of claim 17 wherein the insecticidal compound is 4,6-diamino-1,2-dihydro-2,2-dimethyl-1-cycloheptylmethoxy)-1,3,5-triazine hydrobromide.

20. The method of claim 17 wherein the insecticidal compound is 4,6-diamino-1,2-dihydro-2,2-dimethyl-1-(2,4,5-trichlorophenylmethoxy)-1,3,5-triazine, pamoic acid salt.

21. The method of claim 17 wherein the insecticidal compound is 4,6-diamino-1,2-dihydro-2,2-dimethyl-1-(5-bromo-2,4-dichlorophenylmethoxy)-1,3,5-triazine, pamoic acid salt.

22. The method of claim 17 wherein the insecticidal compound is 4,6-diamino-1,2-dihydro-2,2-dimethyl-1-(naphth-1-ylmethoxy)-1,3,5-triazine, pentanoic acid salt.

23. The method of claim 17 wherein the insecticidal compound is 4,6-diamino-1,2-dihydro-2,2-dimethyl-1-[3-(2,4-dimethylphenoxy)propoxy]-1,3,5-triazine hydrobromide.

24. The method of claim 17 wherein the insecticidal compound is 4,6-diamino-1,2-dihydro-2,2-dimethyl-1-[3-(2,5-dimethylphenoxy)propoxy]-1,3,5-triazine hydrobromide.

25. The method of claim 17 wherein the insecticidal compound is 4,6-diamino-1,2-dihydro-2,2-dimethyl-1-[3-(2,3,5-trimethylphenoxy)propoxy]-1,3,5-triazine hydrobromide.

26. The method of claim 17 wherein the insecticidal compound is 4,6-diamino-1,2-dihydro-2,2-dimethyl-1-[2-(adamant-1-yl)ethoxy]-1,3,5-triazine hydrobromide.

27. The method of claim 17 wherein the insecticidal compound is 4,6-diamino-1,2-dihydro-2,2-dimethyl-1-(4-bromophenylmethoxy)-1,3,5-triazine hydrobromide.

28. The method of claim 17 wherein the insecticidal compound is 4,6-diamino-1,2-dihydro-2,2-dimethyl-1-[3-(2-bromo-4,5-dichlorophenyl)propoxy]-1,3,5-triazine hydrochloride.

29. Compounds of the formula

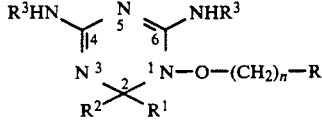

and agriculturally acceptable salts thereof, wherein R is a heterocyclyl moiety selected from the following

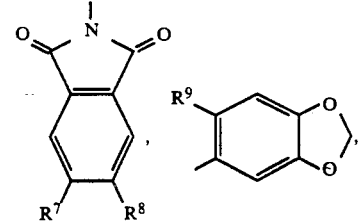

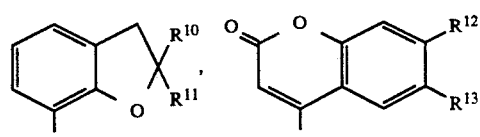

wherein
$R^1$ is selected from the group consisting of lower alkyl, arylalkyl, arylalkenyl, and alkoxyaryl, wherein aryl is phenyl, naphthyl, or phenanthryl;
$R^2$ is selected from the group consisting of hydrogen and methyl;
or $R^1$ and $R^2$ taken together form a spirocycloalkane ring of 3 to 9 carbon atoms;
$R^3$ is selected from the group consisting of hydrogen, lower alkylcarbonyl, cyclopropylcarbonyl, methoxymethylcarbonyl, and 2-furanylcarbonyl; and
$R^7$, $R^8$, $R^9$, $R^{10}$, $R^{11}$, $R^{12}$, and $R^{13}$ are independently hydrogen, halogen, alkyl, or alkoxy with the proviso that $R^7$ and $R^8$ are not both hydrogen and with the further proviso that $R^9$ is not hydrogen, and wherein each alkyl and alkenyl group independently contains up to 13 carbon atoms.

30. 4,6-diamino-1,2-dihydro-2,2-dimethyl-1-[2-(4,5-dichloro-1-phthalimido)ethoxy]-1,3,5-triazine.

31. 4,6-diamino-1,2-dihydro-2,2-dimethyl-1-[2-(4,5-dichloro-1-phthalimido)propoxy]-1,3,5-triazine.

32. Compounds of the formula

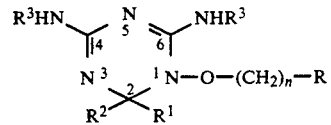

and agriculturally acceptable salts thereof, wherein R is selected from phenyl or naphthyl, phenylalkyl, phenylmethylalkyl, (α-cycloalkyl)phenylmethyl, or (phenyl-substituted)cycloalkyl, wherein each phenyl or naphthyl group optionally is substituted with lower alkyl, halogen, and lower alkoxy and each alkyl is straight or branched, wherein each cycloalkyl group independently contains 3 to 7 carbon atoms;
n is 1 to 5;
$R^1$ is selected from the group consisting of lower alkyl, arylalkyl, arylalkenyl, and alkoxyaryl, wherein aryl is phenyl, naphthyl, or phenanthryl;
$R^2$ is selected from the group consisting of hydrogen and methyl;
or $R^1$ and $R^2$ taken together form a spirocycloalkane ring of 3 to 9 carbon atoms; and
$R^3$ is selected from the group consisting of hydrogen, lower alkylcarbonyl, cyclopropylcarbonyl, methoxymethylcarbonyl, and 2-furanylcarbonyl, with the proviso that $R^3$ is not hydrogen or lower alkylcarbonyl when R is (optionally substituted)phenyl, (optionally substituted)naphthyl, or phenylalkyl, and wherein each alkyl and alkenyl group independently contains up to 13 carbon atoms.

33. 4,6-diamino-1,2-dihydro-2,2-dimethyl-1-[2-methyl-3-(2-fluorophenyl)propoxy]-1,3,5-triazine.

34. 4,6-diamino-1,2-dihydro-2,2-dimethyl-1-[2-methyl-3-(4-methoxyphenyl)propoxy]-1,3,5-triazine.

35. 4,6-diamino-1,2-dihydro-2,2-dimethyl-1-[3-(4-methoxyphenyl)butoxy]-1,3,5-triazine.

36. 4,6-diamino-1,2-dihydro-2,2-dimethyl-1-[cis/-trans-3-(2-methylphenyl)cyclohexylmethoxy]-1,3,5-triazine.

37. 4,6-diamino-1,2-dihydro-2,2-dimethyl-1-[cis-3-(3-methylphenyl)cyclohexylmethoxy]-1,3,5-triazine.

38. 4,6-diamino-1,2-dihydro-2,2-dimethyl-1-[cis/-trans-3-(4-methylphenyl)cyclohexylmethoxy]-1,3,5-triazine.

39. The compound 4,6-diamino-1,2-dihydro-2,2-dimethyl-1-(3-cyclopropyl-3-phenylpropoxy)-1,3,5-triazine hydrobromide.

40. The compound 4,6-diamino-1,2-dihydro-2,2-dimethyl-1-(cis/trans-3-phenylcyclohexylmethoxy)-1,3,5-triazine hydrobromide.

* * * * *